United States Patent
Lochmuller et al.

(10) Patent No.: US 11,338,045 B2
(45) Date of Patent: May 24, 2022

(54) ADENO-ASSOCIATED VIRUS VECTOR DELIVERY OF A FRAGMENT OF MICRO-DYSTROPHIN TO TREAT MUSCULAR DYSTROPHY

(71) Applicants: NEWCASTLE UNIVERSITY, Newcastle upon Tyne (GB); University of Heidelberg, Heidelberg (DE)

(72) Inventors: Hanns Lochmuller, Newcastle Upon Tyne (GB); Oliver Muller, Heidelberg (DE)

(73) Assignees: NEWCASTLE UNIVERSITY, Newcastle upon Tyne (GB); University of Heidelberg, Heidelberg (DE)

(*) Notice: Subject to any disclaimer, the term of this patent is extended or adjusted under 35 U.S.C. 154(b) by 59 days.

(21) Appl. No.: 16/494,645

(22) PCT Filed: Mar. 16, 2018

(86) PCT No.: PCT/IB2018/001201
§ 371 (c)(1),
(2) Date: Sep. 16, 2019

(87) PCT Pub. No.: WO2019/012336
PCT Pub. Date: Jan. 17, 2019

(65) Prior Publication Data
US 2020/0078473 A1 Mar. 12, 2020

Related U.S. Application Data

(60) Provisional application No. 62/473,255, filed on Mar. 17, 2017.

(51) Int. Cl.
*C12N 15/86* (2006.01)
*A61K 48/00* (2006.01)

(52) U.S. Cl.
CPC ........ *A61K 48/005* (2013.01); *A61K 48/0075* (2013.01)

(58) Field of Classification Search
CPC .............. A61K 48/005; A61K 48/0075; C12N 2750/14143; C12N 15/86; C07K 14/4707
See application file for complete search history.

(56) References Cited

U.S. PATENT DOCUMENTS

| | | |
|---|---|---|
| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,566,118 B1 | 5/2003 | Atkinson et al. |
| 7,282,199 B2 | 10/2007 | Gao et al. |
| 7,790,449 B2 | 9/2010 | Gao et al. |
| 10,166,272 B2 | 1/2019 | Dickson et al. |
| 2008/0044393 A1 | 2/2008 | White et al. |
| 2019/0117795 A1 | 4/2019 | Rodino-Klapac et al. |
| 2019/0167762 A1 | 6/2019 | Dickson et al. |

FOREIGN PATENT DOCUMENTS

| | | | |
|---|---|---|---|
| JP | 11-318467 A | 11/1999 | |
| JP | 11318467 A | * 11/1999 | ............. C12N 15/09 |
| WO | 1995/13365 A1 | 5/1995 | |
| WO | 1995/13392 A1 | 5/1995 | |
| WO | 1996/17947 A1 | 6/1996 | |
| WO | 1997/06243 A1 | 2/1997 | |
| WO | 1997/08298 A1 | 3/1997 | |
| WO | 1997/09441 A2 | 3/1997 | |
| WO | 1997/21825 A1 | 6/1997 | |
| WO | 1998/09657 A2 | 3/1998 | |
| WO | 1999/11764 A2 | 3/1999 | |
| WO | 2001/83692 A2 | 11/2001 | |
| WO | 2002/53703 A2 | 7/2002 | |
| WO | 2013/016352 A1 | 1/2013 | |
| WO | 2015/197232 A1 | 12/2015 | |
| WO | 2015/197869 A1 | 12/2015 | |
| WO | 2016/177911 A1 | 11/2016 | |
| WO | 2017/165859 A1 | 9/2017 | |

OTHER PUBLICATIONS

Love et al., An autosomal transcript in skeletal muscle with homology to dystrophin., Nature, 339:55-58 (1989).
Mader et al., A steroid-inducible promoter for the controlled overexpression of cloned genes in eukaryotic cells, Proc Natl. Acad. Sci. USA., 90:5603-5607 (1993).
Marsic et al., Vector design Tour de Force: integrating combinatorial and rational approaches to derive novel adeno-associated virus variants, Mol. Ther., 22(11):1900-1909 (2014).
McLaughlin et al., Adeno-associated virus general transduction vectors: analysis of proviral structures, J. Virol., 62:1963-1973 (1988).
Mendell et al., A phase 1/2a follistatin gene therapy trial for becker muscular dystrophy, Molecular Therapy : The Journal of the American Society of Gene Therapy, 23:192-201 (2015).
Mendell et al., Limb-girdle muscular dystrophy type 2D gene therapy restores alpha-sarcoglycan and associated proteins, Ann. Neurol., 66:290-297 (2009).
Mendell et al., Sustained alpha-sarcoglycan gene expression after gene transfer in limb-girdle muscular dystrophy, type 2D, Ann. Neurol., 68:629-638 (2010).
Mori et al., Two novel adeno-associated viruses from cynomolgus monkey: pseudotyping characterization of capsid protein, Virology, 330(2):375-383 (2004).

(Continued)

*Primary Examiner* — Antonio Galisteo Gonzalez
*Assistant Examiner* — Khaleda B Hasan
(74) *Attorney, Agent, or Firm* — Marshall, Gerstein & Borun LLP

(57) ABSTRACT

The invention provides gene therapy vectors, such as adeno-associated vims (AAV) vectors, expressing a functional fragment of the miniaturized human micro-dystrophin gene and method of using these vectors to express the fragment of micro-dystrophin in skeletal muscles including diaphragm and cardiac muscle and to protect muscle fibers from injury, increase muscle strength and reduce and/or prevent fibrosis in subjects suffering from muscular dystrophy.

18 Claims, 7 Drawing Sheets
Specification includes a Sequence Listing.

(56) References Cited

OTHER PUBLICATIONS

Mulieri et al., Protection of human left ventricular myocardium from cutting injury with 2,3-butanedione monoxime, Circ. Res., 65:1441-1449 (1989).
Murphy et al., Long-term correction of obesity and diabetes in genetically obese mice by a single intramuscular injection of recombinant adeno-associated virus encoding mouse leptin, Proc. Natl. Acad. Sci. USA., 94:13921-13926 (1997).
Muscat et al., Multiple 5'-flanking regions of the human alpha-skeletal actin gene synergistically modulate muscle-specific expression, Mol. Cell. Biol., 7:4089-4099 (1987).
Muzyczka, Use of adeno-associated virus as a general transduction vector for mammalian cells, Curr. Topics in Microbial and Immunol., 158:97-129 (1992).
Nevo et al., The Ras antagonist, farnesylthiosalicylic acid (FTS), decreases fibrosis and improves muscle strength in dy/dy mouse model of muscular dystrophy, PloS one, 6:e18049 (2011).
Paul et al., Increased viral titer through concentration of viral harvests from retroviral packaging lines, Hum. Gene Therapy, 4:609-615 (1993).
Perrin et al., An experimental rabies vaccine produced with a new BHK-21 suspension cell culture process: use of serum free medium and perfusion reactor system, Vaccine, 13:1244-1250 (1995).
Rafael et al., Skeletal muscle-specific expression of a utrophin transgene rescues utrophindystrophin deficient mice, Nat. Genet., 19:79-82 (1998).
Rodino-Klapac et al., A translational approach for limb vascular delivery of the micro-dystrophin gene without high volume or high pressure for treatment of Duchenne muscular dystrophy, J. Transl. Med., 5:45 (2007).
Rodino-Klapac et al., Micro-dystrophin and follistatin co-delivery restores muscle function in aged DMD model, Hum Mol. Gen., 22:4929-4937 (2013).
Rodino-Klapac et al., Persistent expression of FLAG-tagged micro dystrophin in nonhuman primates following intramuscular and vascular delivery, Mol. Ther., 18:109-117 (2010).
Ruffing et al., Mutations in the carboxy terminus of adeno-associated virus 2 capsid proteins affect viral infectivity: lack of an RGD integrin-binding motif, J. Gen. Virol., 75:3385-3392 (1994).
Sacco et al., Short telomeres and stem cell exhaustion model Duchenne muscular dystrophy in mdx/mTR mice, Cell., 143:1059-1071 (2010).
Salva et al., Design of tissue-specific regulatory cassettes for high-level rAAV-mediated expression in skeletal and cardiac muscle, Mol. Ther., 15:320-329 (2007).
Sambrook et al., Molecular cloning: A laboratory manual, 2nd Ed., Cold spring harbor laboratory, (Cold Spring Harbor, N.Y. 1989).
Samulski et al., A recombinant plasmid from which an infectious adeno-associated virus genome can be excised in vitro and its use to study viral replication, J. Virol., 61(10):3096-3101 (1987).
Samulski et al., Cloning of adeno-associated virus into pBR322: rescue of intact virus from the recombinant plasmid in human cells, Proc. Natl. Acad. Sci. USA, 79:2077-2081 (1982).
Samulski et al., Helper-free stocks of recombinant adeno-associated viruses: normal integration does not require viral gene expression, J. Virol., 63:3822-3828 (1989).
Schnepp et al., Highly purified recombinant adeno-associated virus vectors. Preparation and quantitation, Methods Mol., Med., 69:427-443 (2002).
Semenza et al., Hypoxia-inducible nuclear factors bind to an enhancer element located 3' to the human erythropoietin gene, Proc. Natl. Acad. Sci. USA., 88:5680-5684 (1991).
Senapathy et al., Molecular cloning of adeno-associated virus variant genomes and generation of infectious virus by recombination in mammalian cells, J. Biol. Chem., 259:4661-4666 (1984).
Sicinski et al., The molecular basis of muscular dystrophy in the mdx mouse: a point mutation, Science, 244(4912):1578-1580 (1989).
Sondergaard et al., AAV.Dysferlin overlap vectors restore function in dysferlinopathy animal models, Ann. Clin. Transl. Neurol., 2:256-270 (2015).
Squire et al., Prevention of pathology in mdx mice by expression of utrophin: analysis using an inducible transgenic expression system., Hum. Mol. Genet., 11:3333-3344 (2002).
Srivastava et al., Nucleotide sequence and organization of the adeno-associated virus 2 genome, J. Virol., 45:555-564 (1983).
Stedman et al., The mdx mouse diaphragm reproduces the degenerative changes of duchenne muscular dystrophy, Nature, 352:536-539 (1991).
Straub et al., Muscular dystrophies and the dystrophin-glycoprotein complex., Curr. Opin. Neurol., 10:168-175 (1997).
Tinsley et al., Expression of full-length utrophin prevents muscular dystrophy in mdx mice, Nat. Med., 4:1441-1444 (1998).
Tinsley et al., Primary structure of dystrophin-related protein, Nature, 360:591-593 (1992).
Tratschin et al., A human parvovirus, adeno-associated virus, as a eucaryotic vector: transient expression and encapsidation of the procaryotic gene for chloramphenicol acetyltransferase, Mol. Cell. Biol., 4:2072-2081 (1984).
Tratschin et al., Adeno-associated virus vector for high-frequency integration, expression, and rescue of genes in mammalian cells, Mol. Cell. Biol., 5:3251-3260 (1985).
Wallace et al., Mechanisms of muscle degeneration, regeneration, and repair in the muscular dystrophies, Annu. Rev. Physiol., 71:37-57 (2009).
Weintraub et al., The myoD gene family: nodal point during specification of the muscle cell lineage, Science, 251:761-766 (1991).
Xiao et al., Efficient long-term gene transfer into muscle tissue of immunocompetent mice by adeno-associated virus vector, J. Virol., 70:8098-8108 (1996).
Xiao et al., Production of high-titer recombinant adeno-associated virus vectors in the absence of helper adenovirus, J. Virol., 12:2224-2232 (1998).
Zhou et al., Haploinsufficiency of utrophin gene worsens skeletal muscle inflammation and fibrosis in mdx mice, J. Neurol. Sci., 264:106-111 (2008).
Zhou et al., Targeting fibrosis in Duchenne muscular dystrophy, J. Neuropathol. Exp. Neurol., 69:771-776 (2010).
Anderson et al., Nucleic acid hybridisation: A practical approach, Ch. 4, IRL Press Limited (Oxford, England).
Bulfield et al., X chromosome-linked muscular dystrophy (mdx) in the mouse, Proc. Natl. Acad. Sci. U S A., 81(4):1189-1192 (1984).
Carnwath et al., Muscular dystrophy in the mdx mouse: histopathology of the soleus and extensor digitorum longus muscles, J. Neural. Sci., 80:39-54 (1987).
Carter, Adeno-associated virus vectors, Curr. Opin. Biotechnol., 3:1533-539 (1992).
Chao et al., Several log increase in therapeutic transgene delivery by distinct adeno-associated viral serotype vectors, Mol. Ther., 2:619-623 (2000).
Chao et al., Sustained and complete phenotype correction of hemophilia b mice following intramuscular injection of aav1 serotype vectors, Mol. Ther., 4:217-222 (2001).
Chicoine et al., Plasmapheresis Eliminates the Negative Impact of AAV Antibodies on Microdystrophin Gene Expression Following Vascular Delivery, Mol Ther., 22(2): 338-347 (2014).
Clark et al., A stable cell line carrying adenovirus-inducible rep and cap genes allows for infectivity titration of adeno-associated virus vectors, Gene. Ther., 3:1124-1132 (1996).
Clark et al., Highly purified recombinant adeno-associated virus vectors are biologically active and free of detectable helper and wild-type viruses, Hum. Gene. Ther., 10(6):1031-1039 (1999).
Clark et al., Recombinant adeno-associated viral vectors mediate long-term transgene expression in muscle, Hum. Gene Ther., 8:659-669 (1997).
Coulton et al., The mdx mouse skeletal muscle myopathy: I. A histological, morphometric and biochemical investigation, Neuropathol. Appl. Neurobiol., 14:53-70 (1988).

(56) References Cited

OTHER PUBLICATIONS

Cserjesi et al., Myogenin induces the myocyte-specific enhancer binding factor MEF-2 independently of other muscle-specific gene products, Mol. Cell. Biol., 11:4854-4862 (1991).
Cullen et al., Ultrastructure of the skeletal muscle in the X chromosome-linked dystrophic (mdx) mouse, Comparison with Duchenne muscular dystrophy, Acta. Neuropathol., 77:69-81 (1988).
De et al., High levels of persistent expression of alpha1-antitrypsin mediated by the nonhuman primate serotype rh. 10 adeno-associated virus despite preexisting immunity to common human adeno-associated viruses, Mol. Ther., 13:67-76 (2006).
Deconinck et al., Utrophin-dystrophin-deficient mice as a model for Duchenne muscular dystrophy, Cell., 90:717-727 (1997).
Desguerre et al., Endomysial fibrosis in Duchenne muscular dystrophy: a marker of poor outcome associated with macrophage alternative activation, J. Neuropathol. Exp Neurol., 68:762-773 (2009).
Diprimio et al., Adeno-associated virus for the treatment of muscle diseases: toward clinical trials, Curr. Opin. Mol. Ther., 12:553-560 (2010).
Dupont-Versteegden et al., Differential expression of muscular dystrophy in diaphragm versus hindlimb muscles of mdx mice, Muscle. Nerve., 15:1105-1110 (1992).
European U.S. Appl. No. 17/783,236, European Search Report and Opinion, dated Oct. 24, 2019.
Flotte et al., Gene Expression from Adeno-associated Virus Vectors in Airway Epithelial Cells, Am. J. Respir. Cell Mol. Biol., 7:349-356, (1992).
Gao et al., Clades of Adeno-associated viruses are widely disseminated in human tissues, J. Virol., 78:6381-6388 (2004).
GenBank Accession No. AF085716, Version AF085716, Adeno-associated virus 5 DNA binding trs helicase (Rep22) and capsid protein (VP1) genes, complete cds, last updated Feb. 9, 1999, located at < https://www.ncbi.nlm.nih.gov/nuccore/AF085716 >.
GenBank Accession No. AX753246, Version AX753246, Sequence 1 from Patent EP1310571, last updated Jun. 23, 2003, located at < https://www.ncbi.nlm.nih.gov/nuccore/AX753246 >.
GenBank Accession No. NC_001829, Version NC_001829, Adeno-associated virus—4, complete genome, complete cds, last updated Aug. 13, 2018, located at < https://www.ncbi.nlm.nih.gov/nuccore/NC_001829 >.
GenBank Accession No. NC_001862, Version NC_001862, Adeno-associated virus 6, complete genome, last updated Jan. 12, 2004, located at < https://www.ncbi.nlm.nih.gov/nuccore/NC_001862.1?report=genbank >.
GenBank Accession No. NC_002077, Version NC_002077, Adeno-associated virus—1, complete genome, last updated Aug. 13, 2018, located at < https://www.ncbi.nlm.nih.gov/nuccore/NC_002077 >.
Grady et al., Skeletal and cardiac myopathies in mice lacking utrophin and dystrophin: a model for Duchenne muscular dystrophy, Cell., 90:729-738 (1997).
Grose et al., Homologous recombination mediates functional recovery of dysferlin deficiency following AAV6 gene transfer, PloS one, 1:e39233 (2012).
Gutpell et al., Skeletal muscle fibrosis in the mdx/utm+/− Mouse validates its suitability as a murine model of duchenne muscular dystrophy, PloS one, 10:e0117306 (2015).
Harper et al., Modular flexibility of dystrophin: implications for gene therapy of duchenne muscular dystrophy, Nat. Med., 8:253-261 (2002).

Hayashita-Kinoh et al., Intra-Amniotic rAAV-Mediated Microdystrophin Gene Transfer Improves Canine X-Linked Muscular Dystrophy and May Induce Immune Tolerance, Mol. Ther., 23(4):627-637 (2015).
Heller et al., 379. MicroRNA-29 and Micro-Dystrophin Combinatorial Therapy Suppresses Fibrosis and Restores Function to mdx/utm+/− Mice, Mol. Ther., 24(1): S151 (2016).
Heller et al., MicroRNA-29 overexpression by adeno-associated virus suppresses fibrosis and restores muscle function in combination with micro-dystrophin, JCI Insight., 2(9): 1-13 (2017).
Hermonat et al., Use of adeno-associated virus as a mammalian DNA cloning vector: transduction of neomycin resistance into mammalian tissue culture cells, Proc. Natl. Acad. Sci. USA, 81:6466-6470 (1984).
Herzog et al., Stable gene transfer and expression of human blood coagulation factor IX after intramuscular injection of recombinant adeno-associated virus, Proc. Natl. Acad. Sci. USA., 94:5804-5809 (1997).
Hoffman et al., Dystrophin: the protein product of the duchenne muscular dystrophy locus, Cell., 51:919-928 (1987).
International Preliminary Report on Patentability for Corresponding International Application No. PCT/IB18/001201, dated Sep. 26, 2019.
International Preliminary Report on Patentability for Corresponding International Application No. PCT/US18/22881, dated Jan. 7, 2020, 51 pages.
International Search Report and Written Opinion for Corresponding International Application No. PCT/IB2018/001201, dated Feb. 5, 2019.
International Search Report and Written Opinion for Corresponding International Application No. PCT/US18/22881, dated May 22, 2018, 12 pages.
Jaynes et al., Transcriptional Regulation of the Muscle Creatine Kinase Gene and Regulated Expression in Transfected Mouse Myoblasts, Mol. Cell. Biol., 6 (8): 2855-64 (1986).
Johnson et al., Muscle creatine kinase sequence elements regulating skeletal and cardiac muscle expression in transgenic mice, Mol. Cell. Biol., 9:3393-3399 (1989).
Kawecka et al., Adeno-Associated Virus (AAV) Mediated Dystrophin Gene Transfer Studies and Exon Skipping Strategies for Duchenne Muscular Dystrophy (DMD), Curr. Gene. Ther., 15(4):395-415 (2015).
Kessler et al., Gene delivery to skeletal muscle results in sustained expression and systemic delivery of a therapeutic protein, Proc. Nat. Acad. Sc. USA, 93:14082-14087 (1996).
Koo et al., Long-term functional adeno-associated virus-microdystrophin expression in the dystrophic CXMDj dog, J. Gene. Med., 13(9):497-506(2011).
Laughlin et al., Cloning of infectious adeno-associated virus genomes in bacterial plasmids, Gene., 23:65-73 (1983).
Lebkowski et al., Adeno-Associated Virus: a Vector System for Efficient Introduction and Integration of DNA into a Variety of Mammalian Cell Types, Molecular and Cellular Biology, 8:3988-3996, (1988).
Lederfein et al., Kilodalton Protein is a Major Product of the Duchenne Muscular Dystrophy Gene in Brain and Other Nonmuscle Tissues, Proc. Natl. Acad. Sci. USA., 89(12):5346-5350 (1992).
Lewis et al., Generation of neutralizing activity against human immunodeficiency virus type 1 in serum by antibody gene transfer, J. Virol., 76:8769-8775 (2002).
Liu et al., Adeno-associated virus-mediated microdystrophin expression protects young mdx muscle from contraction-induced injury, Mol. Ther., 11:245-256 (2005).

* cited by examiner $1 \times 10^{11}$ vg        $3 \times 10^{11}$ vg

Table 1

| Muscle | Mean | SD |
|---|---|---|
| Tibialis Anterior (TA) | 55.49% | 8.45% |
| Gastrocnemius (GAS) | 55.55% | 6.32% |
| Diaphragm | 46.59% | 7.17% |
| Gluteus | 64.83% | 4.80% |
| Psoas | 50.26% | 4.28% |
| Quadriceps | 62.55% | 5.05% |
| Triceps | 56.50% | 7.09% |
| Heart | 100% | 0.00% |

Figure 5

SEQ ID NO: 2 rAAVrh74.MHCK7.C-term.microdystrophin

Main features:
MHCK7 promoter
Chimeric intron sequence
micro-dystrophin C-term sequence (SEQ ID NO: 1)
Poly A tail
Ampicillin resistance
pGEX plasmid backbone with pBR322 origin or replication ATCTATGTCTAGAGTTTAAACaagcttgcatgtctaagctagaccettcagattaaaaataactgaggtaagggcctgggta
ggggaggtggtgtgagacgctcctgtctctcctctatctgcccatcggcccttggggaggaggaatgtgcccaaggactaaaaaaa
ggccatggagccagaggggcgagggcaacagaccttttcatgggcaaaccttggggccctgctgtctagcatgccccactacgggtc
taggctgcccatgtaaggaggcaaggcctggggacacccgagatgcctggttataattaacccagacatgtggctgcccccccccc
ccaacacctgctgcctctaaaaataaccctgtccctggtggatcccctgcatgcgaagatcttcgaacaaggctgtgggggactgag
ggcaggctgtaacaggcttgggggccagggcttatacgtgcctgggactcccaaagtattactgttccatgttcccggcgaagggcc
agctgtccccgccagctagactcagcacttagtttaggaaccagtgagcaagtcagcccttggggcagcccatacaaggccatgg
ggctgggcaagctgcacgcctgggtccggggtgggcacggtgcccgggcaacgagctgaaagctcatctgctctcaggggcccctc
cctggggacagcccctcctggctagtcacaccctgtaggctcctctatataacccaggggcacTggTgctgccctcattctaccaca
cctccacagcacagacagacactcaggagcagccagcggcgcgcccAGGTAAGTTTAGTCTTTTTGTCTTTTATTTCA
GGTCCCGGATCCGGTGGTGGTGCAAATCAAAGAACTGCTCCTCAGTGGATGTTGCCTTTACTTCTAG
GCCTGTACGGAAGTGTTACTTCTGCTCTAAAAGCTGCGGAATTGTACCGCGGCCGCatgctttggtggg
aagaagtagaggactgttatgaaagagaagatgttcaaaagaaaacattcacaaaatgggtaaatgcacaattttctaagtttg
ggaagcagcatattgagaacctcttcagtgacctacaggatgggaggcgcctcctagacctcctcgaaggcctgacagggcaaaa
actgccaaaagaaaaaggatccacaagagttcatgccctgaacaatgtcaacaaggcactgcgggttttgcagaacaataatgtt
gatttagtgaatattggaagtactgacatcgtagatggaaatcataaactgactcttggttttgatttggaatataatcctccactgg
caggtcaaaaatgtaatgaaaaatatcatggctggattgcaacaaaccaacagtgaaaagattctcctgagctgggtccgacaat
caactcgtaattatccacaggttaatgtaatcaacttcaccaccagctggtctgatggcctggctttgaatgctctcatccatagtca
taggccagacctatttgactggaatagtgtggtttgccagcagtcagccacacaacgactggaacatgcattcaacatcgccagat
atcaattaggcatagagaaactactcgatcctgaagatgttgataccacctatccagataagaagtccatcttaatgtacatcaca
tcactcttccaagttttgcctcaacaagtgagcattgaagccatccaggaagtggaaatgttgccaaggccacctaaagtgactaa
agaagaacattttcagttacatcatcaaatgcactattctcaacagatcacggtcagtctagcacagggatatgagagaacttctt
cccctaagcctcgattcaagagctatgcctacacacaggctgcttatgtcaccacctctgaccctacacggagcccatttccttcaca
gcatttggaagctcctgaagacaagtcatttggcagttcattgatggagagtgaagtaaacctggaccgttatcaaacagctttag
aagaagtattatcgtggcttctttctgctgaggacacattgcaagcacaaggagagatttctaatgatgtggaagtggtgaaagac
cagtttcatactcatgagggtacatgatggatttgacagccatcagggccgggttggtaatattctacaattgggaagtaagct
gattggaacaggaaaattatcagaagatgaagaaactgaaaacctcagcactctggaagacctgaacaccagatggaagcttct
gcaggtggccgtcgaggaccgagtcaggcagctgcatgaagcccacagggactttggtccagcatctcagcactttcttccacgt
ctgtccagggtccctgggagagagccatctcgccaaacaaagtgccctactatatcaaccacgagactcaaacaacttgctggga
ccatcccaaaatgacagagctctaccagtctttagctgacctgaataatgtcagattctcagcttataggactgccatgaaactccg

Figure 5 (continued)

aagactgcagaaggcccttt tgcttggatctcttgagcctgtcagctgcatgtgatgccttggaccagcacaacctcaagcaaaatg
accagcccatggatatcctgcagattattaattgtttgaccactatttatgaccgcctggagcaagagcacaacaatttggtcaacg
tccctctctgcgtggatatgtgtctgaactggctgctgaatgtttatgatacgggacgaacagggaggatccgtgtcctgtcttttaa
aactggcatcatttccctgtgtaaagcacatttggaagacaagtacagataccttttcaagcaagtggcaagttcaacaggatttt
gtgaccagcgcaggctgggcctccttctgcatgattctatccaaattccaagacagttgggtgaagttgcatcctttggggcagta
acattgagccaagtgtccggagctgcttccaatttgctaataataagccagagatcgaagcggccctcttcctagactggatgaga
ctggaaccccagtccatggtgtggctgcccgtcctgcacagagtggctgctgcagaaactgccaagcatcaggccaaatgtaacat
ctgcaaagagtgtccaatcattggattcaggtacaggagtctaaagcactttaattatgacatctgccaaagctgctttttttctggt
cgagttgcaaaaggccataaaatgcactatcccatggtggaatattgcactccgactacatcaggagaagatgttcgagactttgc
caaggtactaaaaaacaaatttcgaaccaaaaggtattttgcgaagcatccccgaatgggctacctgccagtgcagactgtctta
gaggggacaacatggaaactcccgttactctgatcaacttctggccagtagattctgcgcctgcctcgtccctcagctttcacac
gatgatactcattcacgcattgaacattatgctagcaggctagcagaaatggaaaacagcaatggatcttatctaaatgatagcat
ctctcctaatgagagcatagatgatgaacatttgttaatccagcattactgccaaagtttgaaccaggactcccccctgagccagcc
tcgtagtcctgcccagatcttgatttccttagagagtgaggaaagaggggagctagagagaatcctagcagatcttgaggaagaa
aacaggaatctgcaagcagaatatgaccgtctaaagcagcagcacgaacataaaggcctgtccccactgccgtccctcctgaaa
tgatgcccacctctccccagagtccccgggatgctgagctcattgctgaggccaagctactgcgtcaacacaaaggccgcctggaa
gccaggatgcaaatcctggaagaccacaataaacagctggagtcacagttacacaggctaaggcagctgctggagcaaccccag
gcagaggccaaagtgaatggcacaacggtgtcctctccttctacctctctacagaggtccgacagcagtcagcctatgctgctccg
agtggttggcagtcaaacttcggactccatgggtgaggaagatcttctcagtcctcccccaggacacaagcacagggttagaggag
gtgatggagcaactcaacaactccttccctagttcaagaggaagaaatacccctggaaagccaatgagagaggacacaatGC<u>G</u>
<u>GCCGCAATAAAAGATCTTTATTTTCATTAGATCTGTGTGTTGGTTTTTTGTGTGTGTGTCTAGACAT</u>
<u>GGCTACGTAGATAATTAGCATGGCGGGTTAATCATTAACTACAAGGAACCCCTAGTGATGGAGTTGG</u>
<u>CCACTCCCTCTCTGCGCGCTCGCTCGCTCACTGAGGCCGGGCGACCAAAGGTCGCCCGACGCCCGGG</u>
<u>CTTTGCCCGGGCGGCCTCAGTGAGCGAGCGAGCGCGCNNNNNNCAGCTGGCGTAATAGCGAAGAG</u>
<u>GCCCGCACCGATCGCCCTTCCCAACAGTTGCGCAGCCTGAATGGCGAATGGAAGTTCCAGACGATTG</u>
<u>AGCGTCAAAATGTAGGTATTTCCATGAGCGTTTTTCCTGTTGCAATGGCTGGCGGTAATATTGTTCTG</u>
<u>GATATTACCAGCAAGGCCGATAGTTTGAGTTCTTCTACTCAGGCAAGTGATGTTATTACTAATCAAAG</u>
<u>AAGTATTGCGACAACGGTTAATTTGCGTGATGGACAGACTCTTTTACTCGGTGGCCTCACTGATTATA</u>
<u>AAAACACTTCTCAGGATTCTGGCGTACCGTTCCTGTCTAAAATCCCTTTAATCGGCCTCCTGTTTAGCT</u>
<u>CCCGCTCTGATTCTAACGAGGAAAGCACGTTATACGTGCTCGTCAAAGCAACCATAGTACGCGCCCT</u>
<u>GTAGCGGCGCATTAAGCGCGGCGGGTGTGGTGGTTACGCGCAGCGTGACCGCTACACTTGCCAGCG</u>
<u>CCCTAGCGCCCGCTCCTTTCGCTTTCTTCCCTTCCTTTCTCGCCACGTTCGCCGGCTTTCCCCGTCAAGC</u>
<u>TCTAAATCGGGGGCTCCCTTTAGGGTTCCGATTTAGTGATTTACGGCACCTCGACCCCAAAAAACTTG</u>
<u>ATTAGGGTGATGGTTCACGTAGTGGGCCATCGCCCTGATAGACGGTTTTTCGCCCTTTGACGTTGGA</u>
<u>GTCCACGTTCTTTAATAGTGGACTCTTGTTCCAAACTGGAACAACACTCAACCCTATCTCGGTCTATTC</u>
<u>TTTTGATTTATAAGGGATTTTGCCGATTTCGGCCTATTGGTTAAAAAATGAGCTGATTTAACAAAAAT</u>
<u>TTAACGCGAATTTTAACAAAATATTAACGTTTACAATTTAAATATTTGCTTATACAATCTTCCTGTTTTT</u>
<u>GGGGCTTTTCTGATTATCAACCGGGGTACATATGATTGACATGCTAGTTTTACGATTACCGTTCATCG</u>
<u>ATTCTCTTGTTTGCTCCAGACTCTCAGGCAATGACCTGATAGCCTTTGTAGAGACCTCTCAAAAATAG</u>
<u>CTACCCTCTCCGGCATGAATTTATCAGCTAGAACGGTTGAATATCATATTGATGGTGATTTGACTGTC</u>
<u>TCCGGCCTTTCTCACCCGTTTGAATCTTTACCTACACATTACTCAGGCATTGCATTTAAATATATGAG</u>
<u>GGTTCTAAAAATTTTTATCCTTGCGTTGAAATAAAGGCTTCTCCCGCAAAAGTATTACAGGGTCATAA</u>
<u>TGTTTTTGGTACAACCGATTTAGCTTTATGCTCTGAGGCTTTATTGCTTAATTTGCTAATTCTTTGCCT</u>

Figure 5 (continued)

TGCCTGTATGATTTATTGGATGTTGGAAGTTCCTGATGCGGTATTTTCTCCTTACGCATCTGTGCGGTA
TTTCACACCGCATATGGTGCACTCTCAGTACAATCTGCTCTGATGCCGCATAGTTAAGCCAGCCCCGA
CACCCGCCAACACCCGCTGACGCGCCCTGACGGGCTTGTCTGCTCCCGGCATCCGCTTACAGACAAG
CTGTGACCGTCTCCGGGAGCTGCATGTGTCAGAGGTTTTCACCGTCATCACCGAAACGCGCGAGACG
AAAGGGCCTCGTGATACGCCTATTTTTATAGGTTAATGTCATGATAATAATGGTTTCTTAGACGTCAG
GTGGCACTTTTCGGGGAAATGTGCGCGGAACCCCTATTTGTTTATTTTTCTAAATACATTCAAATATGT
ATCCGCTCATGAGACAATAACCCTGATAAATGCTTCAATAATATTGAAAAAGGAAGAGTATGAGTAT
TCAACATTTCCGTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACATCGAACTGGAT
CTCAACAGCGGTAAGATCCTTGAGAGTTTTCGCCCCGAAGAACGTTTTCCAATGATGAGCACTTTTAA
AGTTCTGCTATGTGGCGCGGTATTATCCCGTATTGACGCCGGGCAAGAGCAACTCGGTCGCCGCATA
CACTATTCTCAGAATGACTTGGTTGAGTACTCACCAGTCACAGAAAAGCATCTTACGGATGGCATGA
CAGTAAGAGAATTATGCAGTGCTGCCATAACCATGAGTGATAACACTGCGGCCAACTTACTTCTGAC
AACGATCGGAGGACCGAAGGAGCTAACCGCTTTTTTGCACAACATGGGGGATCATGTAACTCGCCTT
GATCGTTGGGAACCGGAGCTGAATGAAGCCATACCAAACGACGAGCGTGACACCACGATGCCTGTA
GCAATGGCAACAACGTTGCGCAAACTATTAACTGGCGAACTACTTACTCTAGCTTCCCGGCAACAATT
AATAGACTGGATGGAGGCGGATAAAGTTGCAGGACCACTTCTGCGCTCGGCCCTTCCGGCTGGCTG
GTTTATTGCTGATAAATCTGGAGCCGGTGAGCGTGGGTCTCGCGGTATCATTGCAGCACTGGGGCCA
GATGGTAAGCCCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGACCAAGTTTACT
CATATATACTTTAGATTGATTTAAAACTTCATTTTTAATTTAAAAGGATCTAGGTGAAGATCCTTTTTG
ATAATCTCATGACCAAAATCCCTTAACGTGAGTTTTCGTTCCACTGAGCGTCAGACCCCGTAGAAAAG
ATCAAAGGATCTTCTTGAGATCCTTTTTTTCTGCGCGTAATCTGCTGCTTGCAAACAAAAAAACCACC
GCTACCAGCGGTGGTTTGTTTGCCGGATCAAGAGCTACCAACTCTTTTTCCGAAGGTAACTGGCTTCA
GCAGAGCGCAGATACCAAATACTGTCCTTCTAGTGTAGCCGTAGTTAGGCCACCACTTCAAGAACTCT
GTAGCACCGCGTACATACCTCGCTCTGCTAATCCTGTTACCAGTGGCTGCTGCCAGTGGCGATAAGTC
GTGTCTTACCGGGTTGGACTCAAGACGATAGTTACCGGATAAGGCGCAGCGGTCGGGCTGAACGGG
GGGTTCGTGCACACAGCCCAGCTTGGAGCGAACGACCTACACCGAACTGAGATACCTACAGCGTGA
GCTATGAGAAAGCGCCACGCTTCCCGAAGGGAGAAAGGCGGACAGGTATCCGGTAAGCGGCAGGG
TCGGAACAGGAGAGCGCACGAGGGAGCTTCCAGGGGGAAACGCCTGGTATCTTTATAGTCCTGTCG
GGTTTCGCCACCTCTGACTTGAGCGTCGATTTTTGTGATGCTCGTCAGGGGGCGGAGCCTATGGAA
AAACGCCAGCAACGCGGCCTTTTTACGGTTCCTGGCCTTTTGCTGGCCTTTTGCTCACATGTTCTTTCC
TGCGTTATCCCCTGATTCTGTGGATAACCGTATTACCGGGTTTGAGTGAGCTGATACCGCTCGCCGCA
GCCGAACGACCGAGCGCAGCGAGTCAGTGAGCGACCAAGCGGAAGAGCGCCCAATACGCAAACCG
CCTCTCCCCGCGCGTTGGCCGATTCATTAATGCAGCTGNNNNNNGCGCGCTCGCTCGCTCACTGAGG
CCGCCCGGGCAAAGCCCGGGCGTCGGGCGACCTTTGGTCGCCCGGCCTCAGTGAGCGAGCGAGCG
CGCAGAGAGGGAGTGGCCAACTCCATCACTAGGGGTTCCTTGTAGTTAATGATTAACCCGCCATGCT
AATTATCTACGTAGCCATGTCT

ADENO-ASSOCIATED VIRUS VECTOR DELIVERY OF A FRAGMENT OF MICRO-DYSTROPHIN TO TREAT MUSCULAR DYSTROPHY

This application claims priority to U.S. Provisional Patent Application No. 62/473,255, filed Mar. 17, 2017 which is incorporated by reference herein in its entirety.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 50217A_Seqlisting.txt; Size: 17,751 bytes, created; Mar. 13, 2018.

FIELD OF INVENTION

The invention provides gene therapy vectors, such as adeno-associated virus (AAV) vectors, expressing a functional fragment of the miniaturized human micro-dystrophin gene and method of using these vectors to express the fragment of micro-dystrophin in skeletal muscles including diaphragm and cardiac muscle and to protect muscle fibers from injury, increase muscle strength and reduce and/or prevent fibrosis in subjects suffering from muscular dystrophy.

BACKGROUND

The importance of muscle mass and strength for daily activities, such as locomotion and breathing, and for whole body metabolism is unequivocal. Deficits in muscle function produce muscular dystrophies (MDs) that are characterized by muscle weakness and wasting and have serious impacts on quality of life. The most well-characterized MDs result from mutations in genes encoding members of the dystrophin-associated protein complex (DAPC). These MDs result from membrane fragility associated with the loss of sarcolemmal-cytoskeleton tethering by the DAPC. Duchenne Muscular Dystrophy (DMD) is one of the most devastating muscle disease affecting 1 in 5000 newborn males.

DMD is caused by mutations in the DMD gene leading to reductions in mRNA and the absence of dystrophin, a 427 kD sarcolemmal protein associated with the dystrophin-associated protein complex (DAPC) (Hoffman et al., *Cell* 51(6): 919-28, 1987). The DAPC is composed of multiple proteins at the muscle sarcolemma that form a structural link between the extra-cellular matrix (ECM) and the cytoskeleton via dystrophin, an actin binding protein, and alpha-dystroglycan, a laminin-binding protein. These structural links act to stabilize the muscle cell membrane during contraction and protect against contraction-induced damage. With dystrophin loss, membrane fragility results in sarcolemmal tears and an influx of calcium, triggering calcium-activated proteases and segmental fiber necrosis (Straub et al., *Curr Opin. Neurol.* 10(2): 168-75, 1997). This uncontrolled cycle of muscle degeneration and regeneration ultimately exhausts the muscle stem cell population (Sacco et al., *Cell*, 2010. 143(7): p. 1059-71; Wallace et al., *Annu Rev Physiol*, 2009. 71: p. 37-57), resulting in progressive muscle weakness, endomysial inflammation, and fibrotic scarring.

Without membrane stabilization from dystrophin or a micro-dystrophin, DMD will manifest uncontrolled cycles of tissue injury and ultimately replace lost muscle fibers with fibrotic scar tissue through connective tissue proliferation. Fibrosis is characterized by the excessive deposits of ECM matrix proteins, including collagen and elastin. ECM proteins are primarily produced from cytokines such as TGFβ that is released by activated fibroblasts responding to stress and inflammation. Although the primary pathological feature of DMD is myofiber degeneration and necrosis, fibrosis as a pathological consequence has equal repercussions. The over-production of fibrotic tissue restricts muscle regeneration and contributes to progressive muscle weakness in the DMD patient. In one study, the presence of fibrosis on initial DMD muscle biopsies was highly correlated with poor motor outcome at a 10-year follow-up (Desguerre et al., *J Neuropathol Exp Neurol*, 2009. 68(7): p. 762-7). These results point to fibrosis as a major contributor to DMD muscle dysfunction and highlight the need for early intervention prior to overt fibrosis.

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the nucleotide sequence of the AAV serotype 2 (AAV2) genome is presented in Srivastava et al., *J Virol*, 45: 555-564 (1983) as corrected by Ruffing et al., *J Gen Virol*, 75: 3385-3392 (1994). As other examples, the complete genome of AAV-1 is provided in GenBank Accession No. NC_002077; the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004). Cloning of the AAVrh.74 serotype is described in Rodino-Klapac., et al. *Journal of Translational Medicine* 5, 45 (2007). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (e.g., at AAV2 nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° C. to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., *Hum Gene Ther,* 8: 659-669 (1997); Kessler et al., *Proc Nat. Acad Sc. USA,* 93: 14082-14087 (1996); and Xiao et al., *J Virol,* 70: 8098-8108 (1996). See also, Chao et al.,*Mol Ther,* 2: 619-623 (2000) and Chao et al., *Mol Ther,* 4: 217-222 (2001). Moreover, because muscle is highly vascularized, recombinant AAV transduction has resulted in the appearance of transgene products in the systemic circulation following intramuscular injection as described in Herzog et al., *Proc Natl Acad Sci USA,* 94: 5804-5809 (1997) and Murphy et al., *Proc Natl Acad Sci USA,* 94: 13921-13926 (1997). Moreover, Lewis et al., *J Virol,* 76: 8769-8775 (2002) demonstrated that skeletal myofibers possess the necessary cellular factors for correct antibody glycosylation, folding, and secretion, indicating that muscle is capable of stable expression of secreted protein therapeutics.

Functional improvement in patients suffering from DMD and other muscular dystrophies requires gene restoration at an early stage of disease. There is a need for treatments that increase muscle strength and protect against muscle injury in patients suffering from DMD.

SUMMARY OF INVENTION

The present invention is directed to gene therapy vectors, e.g. AAV, expressing a functional fragment of the micro-dystrophin protein to skeletal muscles including diaphragm and cardiac muscle to protect muscle fibers from injury, increase muscle strength and reduce and/or prevent fibrosis. The invention provides for therapies and approaches for increasing muscular force and/or increasing muscle mass using gene therapy vectors to deliver a functional fragment of micro-dystrophin to address the gene defect observed in DMD.

In one embodiment, the invention provides for a rAAV vector comprising the nucleotide sequence of SEQ ID NO: 1. The nucleotide sequence of SEQ ID NO: 1 is a functional micro-dystrophin containing a large rod deletion. It retains hinges 1 and 4 and spectrin repeat 24. It also contains the C-terminal fragment of dystrophin. The functional activity of the micro-dystrophin protein is to provide stability to the muscle membrane during muscle contraction, e.g. micro-dystrophin acts as a shock absorber during muscle contraction.

The invention provides for a recombinant AAV vector comprising the functional fragment of the micro-dystrophin nucleotide sequence of SEQ ID NO: 1 and the MHCK7 promoter nucleotide sequence of SEQ ID NO: 3.

The invention also provides for a recombinant AAV vector comprising the pAAV.MHCK7.micro-dystrophin.C-term construct nucleotide sequence of SEQ ID NO: 2.

The term "muscle-specific control element" refers to a nucleotide sequence that regulates expression of a coding sequence that is specific for expression in muscle tissue. These control elements include enhancers and promoters, The invention provides for constructs comprising the muscle-specific control element MHCK7 promoter, the MCK promoter and the MCK enhancer.

In one aspect, the invention provides for a rAAV vector comprising a muscle-specific control element and the functional fragment of the micro-dystrophin gene. For example, the muscle-specific control element is a human skeletal actin gene element, cardiac actin gene element, myocyte-specific enhancer binding factor (MEF), muscle creatine kinase (MCK), truncated MCK (tMCK), myosin heavy chain (MHC), hybrid α-myosin heavy chain enhancer-/MCK enhancer-promoter (MHCK7), C5-12, murine creatine kinase enhancer element, skeletal fast-twitch troponin c gene element, slow-twitch cardiac troponin C gene element, the slow-twitch troponin I gene element, hypoxia-inducible nuclear factors, steroid-inducible element or glucocorticoid response element (GRE).

For example, the muscle specific control element is the MHCK7 promoter nucleotide sequence SEQ ID NO: 3 or the muscle-specific control element is MCK nucleotide sequence SEQ ID NO: 4. In addition, in any of the rAAV vectors of the invention, the muscle-specific control element nucleotide sequence, e.g. MHCK7 or MCK nucleotide sequence, is operably linked to the nucleotide sequence encoding the micro-dystrophin protein. For example, the MHCK7 promoter nucleotide sequence (SEQ ID NO: 3) is operably linked to the functional fragment of the human micro-dystrophin gene (SEQ ID NO: 1) as set out in the construct provided in FIG. 1 or FIG. 5 (SEQ ID NO: 2). The MCK promoter nucleotide sequence (SEQ ID NO: 4) is operably linked to the functional fragment of the human micro-dystrophin gene (SEQ ID NO: 1).

In a further aspect, the invention provides for a rAAV vector comprising the nucleotide sequence of SEQ ID NO: 2 and shown in FIG. 1. This rAAV vector comprises the MHCK7 promoter, a chimeric intron sequence, the coding sequence for a functional fragment of the human micro-dystrophin gene, polyA, ampicillin resistance and the pGEX plasmid backbone with pBR322 origin or replication.

The rAAV vectors of the invention may be any AAV serotype, such as the serotype AAVrh.74, AAV1, AAV2, AAV4, AAVS, AAV6, AAV7, AAV8, AAV9, AAV10, AAV11, AAV12 or AAV13.

The invention also provides for pharmaceutical compositions (or sometimes referred to herein as simply "compositions") comprising any of the rAAV vectors of the invention.

In another embodiment, the invention provides for methods of producing a rAAV vector particle comprising culturing a cell that has been transfected with any rAAV vector of the invention and recovering rAAV particles from the supernatant of the transfected cells. The invention also provides for viral particles comprising any of the recombinant AAV vectors of the invention.

The invention provides for methods of treating muscular dystrophy comprising administering a therapeutically effective amount of any of the recombinant AAV vector of the invention expressing a functional fragment of human micro-dystrophin gene.

The invention provides for methods of treating muscular dystrophy comprising administering a therapeutically effective amount of a recombinant AAV vector comprising the functional fragment of human micro-dystrophin nucleotide sequence of SEQ ID NO: 1 and the MHCK7 promoter nucleotide sequence of SEQ ID NO: 3.

The invention also provides for methods of treating muscular dystrophy comprising administering a therapeutically effective amount of a recombinant AAV vector comprising the construct pAAV.MHCK7.micro-dystrophin.C-term nucleotide sequence of SEQ ID NO: 2. "Fibrosis" refers to the excessive or unregulated deposition of extracellular matrix (ECM) components and abnormal repair processes in tissues upon injury including skeletal muscle, cardiac muscle, liver, lung, kidney, and pancreas. The ECM components that are deposited include fibronectin and collagen, e.g. collagen 1, collagen 2 or collagen 3.

In another embodiment, the invention provides for methods of preventing fibrosis in a subject in need comprising administering a therapeutically effective amount of the any recombinant AAV vector of the invention expresses a functional fragment of the human micro-dystrophin protein targeted to the muscle and enhanced cardiac gene delivery and expression in the heart. For example, any of the rAAV of the invention are administered to subjects suffering from muscular dystrophy to prevent fibrosis, e.g. the rAAV, of the invention expressing a function fragment of the human micro-dystrophin protein administered before fibrosis is observed in the subject.

In addition, the rAAV of the invention expressing a functional fragment of the human micro-dystrophin gene are administered to a subject at risk of developing fibrosis, such as those suffering or diagnosed with muscular dystrophy, e.g. DMD. The rAAV of the invention are administered to the subject suffering from muscular dystrophy in order to prevent new fibrosis in these subjects. These methods may further comprise the step of administering a rAAV expressing micro-dystrophin.

The invention contemplates administering any of the AAV vectors of the invention before fibrosis is observed in the subject. In addition, the rAAV of the invention are administered to a subject at risk of developing fibrosis, such as those suffering or diagnosed with muscular dystrophy, e.g. DMD. The rAAV of the invention are administered to the subject suffering from muscular dystrophy who already has developed fibrosis in order to prevent new fibrosis in these subjects.

The invention also provides for methods of increasing muscular force and/or muscle mass in a subject suffering from muscular dystrophy comprising administering a therapeutically effective amount of any of the rAAV vector of the invention expressing a functional fragment of the human micro-dystrophin gene. These methods may further comprise the step of administering a rAAV expressing a functional fragment of the micro-dystrophin protein.

The invention contemplates administering any of the AAV vectors of the invention to patients diagnosed with DMD before fibrosis is observed in the subject or before the muscle force has been reduced or before the muscle mass has been reduced.

The invention also contemplates administering any of the rAAV of the invention to a subject suffering from muscular dystrophy who already has developed fibrosis, in order to prevent new fibrosis in these subjects. The invention also provides for administering any of the rAAV of the invention to the patient suffering from muscular dystrophy who already has reduced muscle force or has reduced muscle mass in order to protect the muscle from further injury.

In any of the methods of the invention, the subject may be suffering from muscular dystrophy such as DMD or any other dystrophin-associated muscular dystrophy.

In another aspect, the rAAV vectors expressing the micro-dystrophin protein comprises the coding sequence of the micro-dystrophin gene operably linked to a muscle-specific control element other than MHCK7 or MCK. For example, the muscle-specific control element is human skeletal actin gene element, cardiac actin gene element, myocyte-specific enhancer binding factor (MEF), tMCK (truncated MCK), myosin heavy chain (MHC), C5-12 (synthetic promoter), murine creatine kinase enhancer element, skeletal fast-twitch troponin C gene element, slow-twitch cardiac troponin C gene element, the slow-twitch troponin I gene element, hypoxia-inducible nuclear factors, steroid-inducible element or glucocorticoid response element (GRE).

In any of the methods of the invention, the rAAV vector or composition is administered by intramuscular injection or intravenous injection.

In addition, in any of the methods of the invention, the rAAV vector or composition is administered systemically. For examples, the rAAV vector or composition is parentally administration by injection, infusion or implantation.

In another embodiment, the invention provides for composition comprising any of the rAAV vectors of the invention for reducing fibrosis in a subject in need.

In addition, the invention provides for compositions comprising any of the recombinant AAV vectors of the invention for preventing fibrosis in a patient suffering from muscular dystrophy.

The invention provides for compositions comprising any of the recombinant AAV vectors of the invention for treating muscular dystrophy.

The invention provides for compositions comprising a recombinant AAV vector comprising a functional fragment of human micro-dystrophin nucleotide sequence of SEQ ID NO: 1 and the MHCK7 promoter sequence of SEQ ID NO: 3 for treatment of muscular dystrophy.

The invention provides for composition comprising a recombinant AAV vector comprising the construct pAAV.MHCK7.micro-dystrophin.C-term nucleotide sequence of SEQ ID NO: 2 for treatment of muscular dystrophy.

The invention also provides for compositions comprising any of the rAAV vectors of the invention for increasing muscular force and/or muscle mass in a subject suffering from muscular dystrophy. In a further embodiment, the invention provides for compositions comprising any of the rAAV vectors of the invention for treatment of muscular dystrophy.

The compositions of the invention are formulated for intramuscular injection or intravenous injection. The composition of the invention is also formulated for systemic administration, such as parentally administration by injection, infusion or implantation.

In addition, any of the compositions are formulated for administration to a subject suffering from muscular dystrophy such as DMD or any other dystrophin associated muscular dystrophy.

In a further embodiment, the invention provides for use of any of the rAAV vectors of the invention for preparation of a medicament for reducing fibrosis in a subject in need. For example, the subject is in need suffering from muscular dystrophy, such as DMD or any other dystrophin associated muscular dystrophy.

In another embodiment, the invention provides for provides for use of any of the rAAV vectors of the invention for the preparation of a medicament for preventing fibrosis in a subject suffering from muscular dystrophy.

In addition, the invention provides for use of the recombinant AAV vectors of the invention for the preparation of a medicament for increasing muscular strength and/or muscle mass in a subject suffering from muscular dystrophy.

The invention also provides for use of the rAAV vectors of the invention for the preparation of a medicament for treatment of muscular dystrophy.

The invention provides for use of a recombinant AAV vector comprising a fragment of the human micro-dystrophin nucleotide sequence of SEQ ID NO: 1 and the MHCK7 promoter nucleotide sequence of SEQ ID NO: 3 for preparation of a medicament for the treatment of muscular dystrophy.

The invention provides for use of a recombinant AAV vector comprising the construct pAAV.MHCK7.micro-dystrophin.C-term nucleotide sequence of SEQ ID NO: 2 for treatment of muscular dystrophy.

In any of the uses of the invention, the medicament is formulated for intramuscular injection or intravenous injection. In addition, in any of the uses of the invention, the medicament is formulated for systemic administration such as parental administration by injection, infusion or implantation.

Any of the medicaments may be prepared for administration to a subject suffering from muscular dystrophy such as DMD or any other dystrophin associated muscular dystrophy.

BRIEF DESCRIPTION OF DRAWING

FIG. 5 provides the nucleic acid sequence of the rAAVrh74.MHCK7. c-TERMINUS.micro-dystrophin construct (SEQ ID NO: 2).

DETAILED DESCRIPTION

Figure 1:
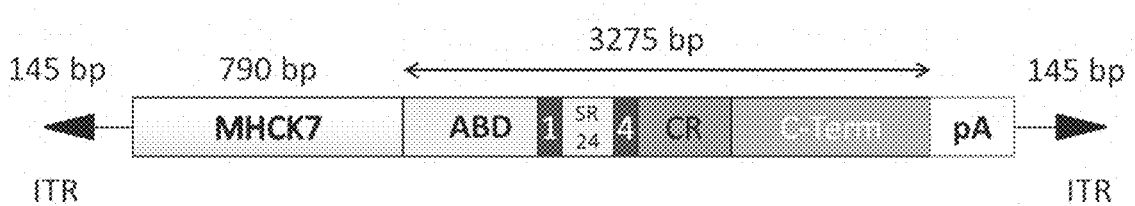
FIG. 1 provides a schematic of the rAAVrh74.MHCK7. c-TERMINUS.micro-dystrophin. This rAAV vector comprises the MHCK7 promoter (790 bp), a chimeric intron sequence, the coding sequence for a functional fragment of the human micro-dystrophin gene, polyA, ampicillin resistance and the pGEX plasmid backbone with pBR322 origin or replication.

The present invention provides for gene therapy vectors, e.g. rAAV vectors, overexpressing a functional fragment of the human micro-dystrophin protein and methods of reducing and preventing fibrosis in muscular dystrophy patients. Muscle biopsies taken at the earliest age of diagnosis of DMD reveal prominent connective tissue proliferation. Muscle fibrosis is deleterious in multiple ways. It reduces normal transit of endomysial nutrients through connective tissue barriers, reduces the blood flow and deprives muscle of vascular-derived nutritional constituents, and functionally contributes to early loss of ambulation through limb contractures. Over time, treatment challenges multiply as a result of marked fibrosis in muscle. This can be observed in muscle biopsies comparing connective tissue proliferation at successive time points. The process continues to exacerbate leading to loss of ambulation and accelerating out of control, especially in wheelchair-dependent patients.

Without early treatment a parallel approach to reduce fibrosis it is unlikely that the benefits of exon skipping, stop-codon read-through or gene replacement therapies can ever be fully achieved. Even small molecules or protein replacement strategies are likely to fail without an approach to reduce muscle fibrosis. Previous work in aged mdx mice with existing fibrosis treated with AAV.micro-dystrophin demonstrated that we could not achieve full functional restoration (Liu, M., et al., *Mol Ther* 11, 245-256 (2005)). It is also known that progression of DMD cardiomyopathy is accompanied by scarring and fibrosis in the ventricular wall.

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector; as such a vector is contained within an AAV vector particle.

AAV

Recombinant AAV genomes of the invention comprise nucleic acid molecule of the invention and one or more AAV ITRs flanking a nucleic acid molecule. AAV DNA in the rAAV genomes may be from any AAV serotype for which a recombinant virus can be derived including, but not limited to, AAV serotypes AAVrh.74, AAV-1, AAV-2, AAV-3, AAV-4, AAV-5, AAV-6, AAV-7, AAV-8, AAV-9, AAV-10, AAV-11, AAV-12 and AAV-13. Production of pseudotyped rAAV is disclosed in, for example, WO 01/83692. Other types of rAAV variants, for example rAAV with capsid mutations, are also contemplated. See, for example, Marsic et al., *Molecular Therapy*, 22(11): 1900-1909 (2014). As noted in the Background section above, the nucleotide sequences of the genomes of various AAV serotypes are known in the art. To promote skeletal muscle-specific expression, AAV1, AAV6, AAV8 or AAVrh.74 may be used.

DNA plasmids of the invention comprise rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell, are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAVrh.74, AAV-8, AAV-9, AAV-10, AAV-11, AAV-12 and AAV-13. Production of pseudotyped rAAV is disclosed in, for example, WO 01/83692 which is incorporated by reference herein in its entirety.

Methods of generating a packaging cell comprise creating a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, *Proc. Natl. Acad. S6*. USA, 79: 2077-2081), addition of synthetic linkers containing restriction endonuclease cleavage sites (Laughlin et al., 1983, *Gene*, 23: 65-73) or by direct, blunt-end ligation (Senapathy & Carter, 1984, *J. Biol. Chem.*, 259: 4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, *Current Opinions in Biotechnology*, 1533-539; and Muzyczka, 1992, *Curr. Topics in Microbial. and Immunol.*, 158: 97-129). Various approaches are described in Ratschin et al., *Mol. Cell. Biol.* 4: 2072 (1984); Hermonat et al., *Proc. Natl. Acad. Sci. USA*, 81: 6466 (1984); Tratschin et al., *Mol. Cell. Biol.* 5: 3251 (1985); McLaughlin et al., *J. Virol.*, 62: 1963 (1988); and Lebkowski et al., *Mol. Cell. Biol.*, 7: 349 (1988). Samulski et al., *J. Virol.*, 63: 3822-3828 (1989); U.S. Pat. No. 5,173,414; WO 95/13365 and corresponding U.S. Pat. No. 5,658,776 ; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. *Vaccine* 13: 1244-1250 (1995); Paul et al. *Human Gene Therapy* 4: 609-615 (1993); Clark et al. *Gene Therapy* 3: 1124-1132 (1996); U.S. Pat. No. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (i.e., infectious encapsidated rAAV particles) of the invention comprise a rAAV genome. In exemplary embodiments, the genomes of both rAAV lack AAV rep and cap DNA, that is, there is no AAV rep or cap DNA between the ITRs of the genomes. Examples of rAAV that may be constructed to comprise the nucleic acid molecules of the invention are set out in International Patent Application No. PCT/US2012/047999 (WO 2013/016352) incorporated by reference herein in its entirety.

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69 427-443 (2002); U.S. Pat. No. 6,566,118 and WO 98/09657.

In another embodiment, the invention contemplates compositions comprising rAAV of the present invention. Compositions of the invention comprise rAAV and a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers and surfactants such as pluronics.

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1 \times 10^6$, about $1 \times 10^7$, about $1 \times 10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg).

Methods of transducing a target cell with rAAV, in vivo or in vitro, are contemplated by the invention. The in vivo methods comprise the step of administering an effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is FSHD.

Combination therapies are also contemplated by the invention. Combination as used herein includes both simultaneous treatment and sequential treatments. Combinations of methods of the invention with standard medical treatments (e.g., corticosteroids) are specifically contemplated, as are combinations with novel therapies.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the micro-dystrophin protein.

The invention provides for local administration and systemic administration of an effective dose of rAAV and compositions of the invention. For example, systemic administration is administration into the circulatory system so that the entire body is affected. Systemic administration includes enteral administration such as absorption through the gastrointestinal tract and parental administration through injection, infusion or implantation.

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

The dose of rAAV to be administered in methods disclosed herein will vary depending, for example, on the particular rAAV, the mode of administration, the treatment goal, the individual, and the cell type(s) being targeted, and may be determined by methods standard in the art. Titers of each rAAV administered may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$, about $1\times10^{14}$, or to about $1\times10^{15}$ or more DNase resistant particles (DRP) per ml. Dosages may also be expressed in units of viral genomes (vg) (i.e., $1\times10^7$ vg, $1\times10^8$ vg, $1\times10^9$ vg, $1\times10^{10}$ vg, $1\times10^{11}$ vg, $1\times10^{12}$ vg, $1\times10^{13}$ vg, $1\times10^{14}$ vg, $1\times10^{15}$ respectively). Dosages may also be expressed in units of viral genomes (vg) per kilogram (kg) of bodyweight (i.e., $1\times10^{10}$ vg/kg, $1\times10^{11}$ vg/kg, $1\times10^{12}$ vg/kg, $1\times10^{13}$ vg/kg, $1\times10^{14}$ vg/kg, $1\times10^{15}$ vg/kg respectively). Methods for titering AAV are described in Clark et al., *Hum. Gene Ther.*, 10: 1031-1039 (1999).

In particular, actual administration of rAAV of the present invention may be accomplished by using any physical method that will transport the rAAV recombinant vector into the target tissue of an animal. Administration according to the invention includes, but is not limited to, injection into muscle, the bloodstream and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical carriers, diluents or excipients suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV of the invention results in sustained expression of the micro-dystrophin protein. The present invention thus provides methods of administering/delivering rAAV which express of micro-dystrophin protein to an animal, preferably a human being. These methods include transducing tissues (including, but not limited to, tissues such as muscle, organs such as liver and brain, and glands such as salivary glands) with one or more rAAV of the present invention. Transduction may be carried out with gene cassettes comprising tissue specific control elements. For example, one embodiment of the invention provides methods of transducing muscle cells and muscle tissues directed by muscle-specific control elements, including, but not limited to, those derived from the actin and myosin gene families, such as from the myoD gene family (See Weintraub et al., *Science,* 251: 761-766 (1991)), the myocyte-specific enhancer binding factor MEF-2 (Cserjesi and Olson, *Mol Cell Biol* 11: 4854-4862 (1991)), control elements derived from the human skeletal actin gene (Muscat et al., *Mol Cell Biol,* 7: 4089-4099 (1987)), the cardiac actin gene, muscle creatine kinase sequence elements (See Johnson et al., *Mol Cell Biol,* 9: 3393-3399 (1989)) and the murine creatine kinase enhancer (mCK) element, control elements derived from the skeletal fast-twitch troponin C gene, the slow-twitch cardiac troponin C gene and the slow-twitch troponin I gene: hypoxia-inducible nuclear factors (Semenza et al., *Proc Natl Acad Sci USA,* 88: 5680-5684 (1991)), steroid-inducible elements and promoters including the glucocorticoid response element (GRE) (See Mader and White, *Proc. Natl. Acad. Sci. USA* 90: 5603-5607 (1993)), and other control elements.

Muscle tissue is an attractive target for in vivo DNA delivery, because it is not a vital organ and is easy to access. The invention contemplates sustained expression of micro-dystrophin from transduced myofibers.

By "muscle cell" or "muscle tissue" is meant a cell or group of cells derived from muscle of any kind (for example, skeletal muscle and smooth muscle, e.g. from the digestive tract, urinary bladder, blood vessels or cardiac tissue). Such muscle cells may be differentiated or undifferentiated, such as myoblasts, myocytes, myotubes, cardiomyocytes and cardiomyoblasts.

The term "transduction" is used to refer to the administration/delivery of the coding region of the micro-dystrophin to a recipient cell either in vivo or in vitro, via a replication-deficient rAAV of the invention resulting in expression of micro-dystrophin by the recipient cell.

Thus, the invention provides methods of administering an effective dose (or doses, administered essentially simultaneously or doses given at intervals) of rAAV that encode micro-dystrophin to a patient in need thereof.

EXAMPLES

Example 1

Generation of the
pAAV.MHCK7.micro-dystrophin.C-terminus
Construct

The pAAV.MHCK7.micro-dystrophin.C-term plasmid contained a human micro-dystrophin cDNA expression cassette flanked by AAV2 inverted terminal repeat sequences (ITR). The micro-dystrophin cassette included the C-terminal domain of dystrophin allowing it to bind to endogenous binding partners (Syntrophins, α-Dystrobrevin, nNOS) important for cell signaling events. Initial work with this cassette was focused on cardiac delivery and utilized an M260 promoter and AAV9. Very good expression and function was achieved in the heart, but very little skeletal muscle expression (Straub & Campbell, *Curr Opin Neurol* 10, 168-175 (1997).

This cassette was cloned it into the AAV2.MHCK7/synthetic polyA backbone to achieve cardiac and skeletal muscle expression (FIG. 1) as described in Sacco et al. *Cell* 143, 1059-1071 (2010), Wallace et al. *Annu Rev Physiol* 71, 37-57 (2009) and Zhou et al. *J Neuropathol Exp Neurol* 69, 771-776 (2010). It was this sequence that was encapsidated into AAVrh.74 virions. This serotype shares 93% amino acid identity with AAV8 and is most similar to a related clade E virus rh.10 described by Wilson and colleagues (Desguerre et al. *J Neuropathol Exp Neurol* 68, 762-773 (2009). The newly cloned micro-dys construct is characterized by an in-frame rod deletion. Hinges 1 and 4 remain but the spectrin-like repeats were removed with the exception of a small fragment of the final repeat (SR24). This allows for a full coding sequence of the N and C termini producing a 125 kDa protein. The micro-dystrophin protein (3,275 bp) is guided by a MHCK7 promoter (790 bp). The total construct size is 8,329 bp. After viral vector production, the micro-dys.c-term construct was tested for potency. The micro-dystrophin cassette has a small 53 bp synthetic polyA signal for mRNA termination.

Previous studies have validated cardiac expression using MHCK7 promoter (Salva et al. *Mol Ther* 15, 320-329 (2007) and AAVrh74 achieving skeletal, diaphragm, and cardiac muscle expression (Sondergaard et al. *Annals of clinical and Transl Neurology* 2, 256-270, 2015). The nucleotide sequence of construct of FIG. 1 was encapsidated into AAVrh.74 virions. The molecular clone of the AAVrh.74 serotype was cloned from a rhesus macaque lymph node and is described in in Rodino-Klapac et al. *Journal of Translational medicine* 5, 45 (2007).

Example 2

Intramuscular Expression Studies Using pAAV.MHCK7.micro-dystrophin.C-terminus

Figure 2:
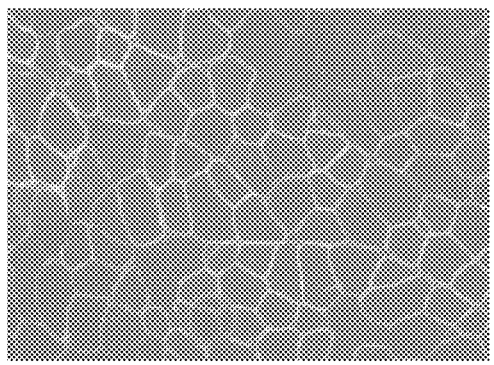
FIG. 2 depicts expression studies after injection into the tibialis anterior muscle in mdx mice at 1×1011 vg or 3×1011 vg. Good expression was observed at both doses.
Figure 2:
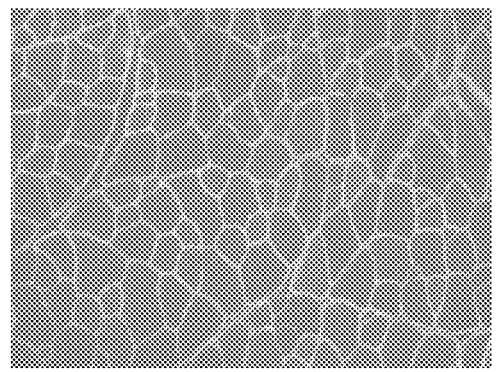
Figure 3:
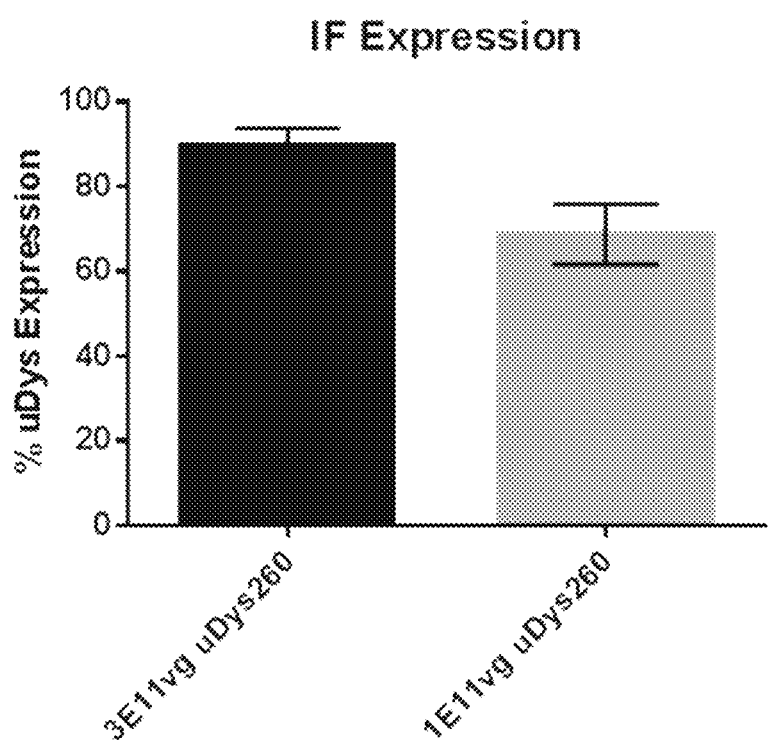
FIG. 3 provides immunohistological staining for dystrophin with the C-terminal polyclonal antibody after injection into the tibialis anterior muscle.

Expression studies were conducted with this human micro-dystrophin containing the C terminus cassette (rAAVrh.74.MHCK7.micro-dys.c-term) by intramuscular injection. The tibialis anterior muscle of mdx mice was injected with $1\times10^{11}$ vg or $3\times10^{11}$ vg (n=5 per group). Six weeks later the muscles were harvested and stained for dystrophin expression with the C-terminal polyclonal antibody. The results of the dose study are presented below in FIG. 2. Comparative dosing at 1e11 and 3e11 vg demonstrates that good gene expression was achieved at both the low and high dose. Immunohistological staining for dystrophin with the C-terminal polyclonal antibody indicated dose dependent expression (FIG. 3).

Example 3

Systemic Delivery of pAAV.MHCK7.micro-dystrophin.C-terminus to mdx Mice

Figure 4:
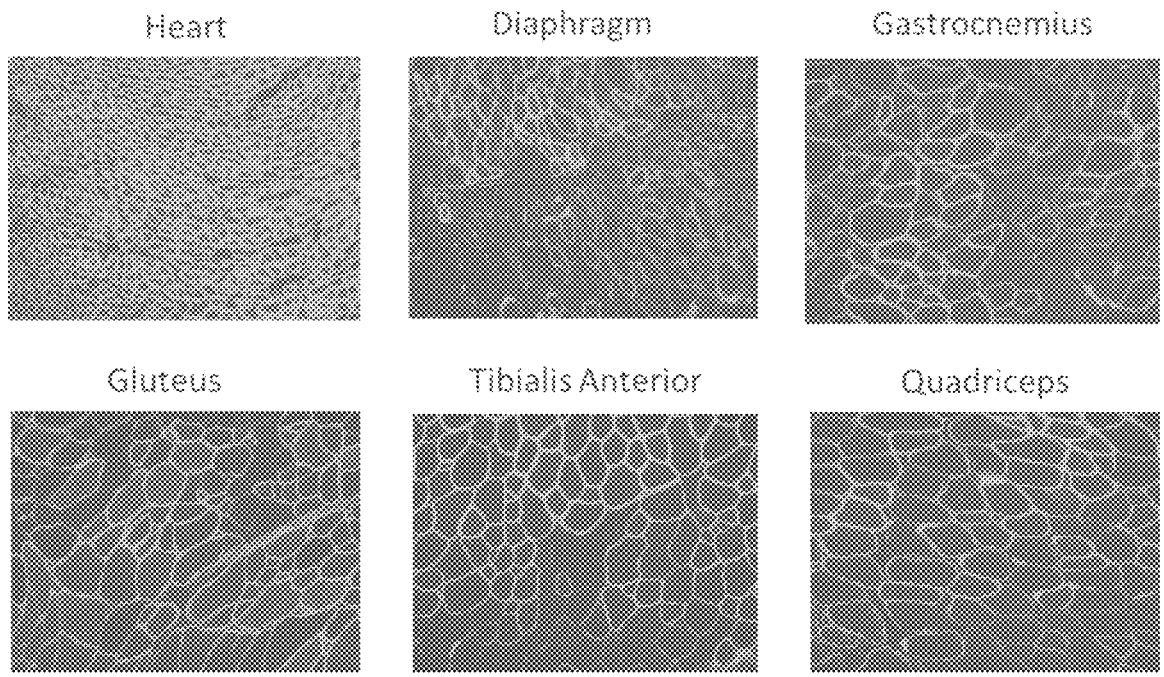
FIG. 4 demonstrates widespread transduction of cardiac muscle fibers after systemic administration of rAAVrh.74.MHCK7.micro-dys.c-term. Table 1. Provides quantification of micro-dys.C-term expression following systemic delivery. 4 random 20× images were counted and expressed as a percentage of positive fibers versus all muscle fibers in the images. Mean±SD of 5 animals.

Cohorts of mdx mice were injected with 6e12 vg (2e14 vg/kg) of rAAVrh.74.MHCK7.micro-dys.c-term. Systemically injected (tail vein) mdx mice (n=5) showed high levels of staining throughout all muscles. FIG. 4 represents the widespread transduction of cardiac muscle fibers after a 6e12 vg systemic dose. Following 6 weeks of treatment, all muscles were harvested and the number of dystrophin positive fibers were quantified (Table 1).

REFERENCES

1. Hoffman, E. P., Brown, R. H., Jr. & Kunkel, L. M. Dystrophin: the protein product of the Duchenne muscular dystrophy locus. *Cell* 51, 919-928 (1987).
2. Straub, V. & Campbell, K. P. Muscular dystrophies and the dystrophin-glycoprotein complex. *Curr Opin Neurol* 10, 168-175 (1997).
3. Sacco, A., et al. Short telomeres and stem cell exhaustion model Duchenne muscular dystrophy in mdx/mTR mice. *Cell* 143, 1059-1071 (2010).
4. Wallace, G. Q. & McNally, E. M. Mechanisms of muscle degeneration, regeneration, and repair in the muscular dystrophies. *Annu Rev Physiol* 71, 37-57 (2009).
5. Zhou, L. & Lu, H. Targeting fibrosis in Duchenne muscular dystrophy. *J Neuropathol Exp Neurol* 69, 771-776 (2010).
6. Desguerre, I., et al. Endomysial fibrosis in Duchenne muscular dystrophy: a marker of poor outcome associated with macrophage alternative activation. *J Neuropathol Exp Neurol* 68, 762-773 (2009).
7. DiPrimio, N., McPhee, S. W. & Samulski, R. J. Adeno-associated virus for the treatment of muscle diseases: toward clinical trials. *Curr Opin Mol Ther* 12, 553-560 (2010).
8. Mendell, J. R., et al. Sustained alpha-sarcoglycan gene expression after gene transfer in limb-girdle muscular dystrophy, type 2D. *Ann Neurol* 68, 629-638 (2010).
9. Mendell, J. R., et al. Limb-girdle muscular dystrophy type 2D gene therapy restores alpha-sarcoglycan and associated proteins. *Ann Neurol* 66, 290-297 (2009).
10. Mendell, J. R., et al. A phase 1/2a follistatin gene therapy trial for becker muscular dystrophy. *Molecular therapy: the journal of the American Society of Gene Therapy* 23, 192-201 (2015).
11. Carnwath, J. W. & Shotton, D. M. Muscular dystrophy in the mdx mouse: histopathology of the soleus and extensor digitorum longus muscles. *J Neurol Sci* 80, 39-54 (1987).
12. Coulton, G. R., Morgan, J. E., Partridge, T. A. & Sloper, J. C. The mdx mouse skeletal muscle myopathy: I. A histological, morphometric and biochemical investigation. *Neuropathol Appl Neurobiol* 14, 53-70 (1988).
13. Cullen, M. J. & Jaros, E. Ultrastructure of the skeletal muscle in the X chromosome-linked dystrophic (mdx) mouse. Comparison with Duchenne muscular dystrophy. *Acta Neuropathol* 77, 69-81 (1988).
14. Dupont-Versteegden, E. E. & McCarter, R. J. Differential expression of muscular dystrophy in diaphragm versus hindlimb muscles of mdx mice. *Muscle Nerve* 15, 1105-1110 (1992).
15. Stedman, H. H., et al. The mdx mouse diaphragm reproduces the degenerative changes of Duchenne muscular dystrophy. *Nature* 352, 536-539 (1991).
16. Deconinck, A. E., et al. Utrophin-dystrophin-deficient mice as a model for Duchenne muscular dystrophy. *Cell* 90, 717-727 (1997).
17. Grady, R. M., et al. Skeletal and cardiac myopathies in mice lacking utrophin and dystrophin: a model for Duchenne muscular dystrophy. *Cell* 90, 729-738 (1997).
18. Love, D. R., et al. An autosomal transcript in skeletal muscle with homology to dystrophin. *Nature* 339, 55-58 (1989).
19. Tinsley, J. M., et al. Primary structure of dystrophin-related protein. *Nature* 360, 591-593 (1992).
20. Tinsley, J., et al. Expression of full-length utrophin prevents muscular dystrophy in mdx mice. *Nat Med* 4, 1441-1444 (1998).
21. Squire, S., et al. Prevention of pathology in mdx mice by expression of utrophin: analysis using an inducible transgenic expression system. *Hum Mol Genet* 11, 3333-3344 (2002).
22. Rafael, J. A., Tinsley, J. M., Potter, A. C., Deconinck, A. E. & Davies, K. E. Skeletal muscle-specific expression of a utrophin transgene rescues utrophin-dystrophin deficient mice. *Nat Genet* 19, 79-82 (1998).
23. Zhou, L., et al. Haploinsufficiency of utrophin gene worsens skeletal muscle inflammation and fibrosis in mdx mice. *J Neurol Sci* 264, 106-111 (2008).

24. Gutpell, K. M., Hrinivich, W. T. & Hoffman, L. M. Skeletal Muscle Fibrosis in the mdx/utrn+/− Mouse Validates Its Suitability as a Murine Model of Duchenne Muscular Dystrophy. *PloS one* 10, e0117306 (2015).
25. Rodino-Klapac, L. R., et al. Micro-dystrophin and follistatin co-delivery restores muscle function in aged DMD model. *Human molecular genetics* 22, 4929-4937 (2013).
26. Nevo, Y., et al. The Ras antagonist, farnesylthiosalicylic acid (FTS), decreases fibrosis and improves muscle strength in dy/dy mouse model of muscular dystrophy. *PloS one* 6, e18049 (2011).
27. Rodino-Klapac, L. R., et al. A translational approach for limb vascular delivery of the micro-dystrophin gene without high volume or high pressure for treatment of Duchenne muscular dystrophy. *J Transl Med* 5, 45 (2007).
28. Mulieri, L. A., Hasenfuss, G., Ittleman, F., Blanchard, E. M. & Alpert, N. R. Protection of human left ventricular myocardium from cutting injury with 2,3-butanedione monoxime. *Circ Res* 65, 1441-1449 (1989).
29. Rodino-Klapac, L. R., et al. Persistent expression of FLAG-tagged micro dystrophin in nonhuman primates following intramuscular and vascular delivery. *Molecular therapy: the journal of the American Society of Gene Therapy* 18, 109-117 (2010).
30. Grose, W. E., et al. Homologous recombination mediates functional recovery of dysferlin deficiency following AAV8 gene transfer. *PloS one* 7, e39233 (2012).
31. Liu, M., et al. Adeno-associated virus-mediated micro-dystrophin expression protects young mdx muscle from contraction-induced injury. *Mol Ther* 11, 245-256 (2005).
32. Harper, S. Q., et al. Modular flexibility of dystrophin: implications for gene therapy of Duchenne muscular dystrophy. *Nature medicine* 8, 253-261 (2002).
33. Rodino-Klapac, L. R., et al. Persistent expression of FLAG-tagged micro dystrophin in nonhuman primates following intramuscular and vascular delivery. *Mol Ther* 18, 109-117 (2010).
34. Salva, M. Z., et al. Design of tissue-specific regulatory cassettes for high-level rAAV-mediated expression in skeletal and cardiac muscle. *Mol Ther* 15, 320-329 (2007).
35. Sondergaard, P. C., et al. AAV.Dysferlin Overlap Vectors Restore Function in Dysferlinopathy Animal Models. *Annals of clinical and translational neurology* 2, 256-270 (2015).
36. De, B. P., et al. High levels of persistent expression of alpha1-antitrypsin mediated by the nonhuman primate serotype rh.10 adeno-associated virus despite preexisting immunity to common human adeno-associated viruses. *Mol Ther* 13, 67-76 (2006).
37. Rodino-Klapac, L. R., et al. A translational approach for limb vascular delivery of the micro-dystrophin gene without high volume or high pressure for treatment of Duchenne muscular dystrophy. *Journal of translational medicine* 5, 45 (2007).
38. Bulfield et al., X chromosome-linked muscular dystrophy (mdx) in the mouse. *Proc Natl Acad Sci USA*. 1984; 81(4): 1189-1192.
39. Sicinski et al., The molecular basis of muscular dystrophy in the mdx mouse: a point mutation. *Science*. 1989 30;244(4912):1578-80

```
                         SEQUENCE LISTING

<110> RESEARCH INSTITUTE AT NATIONWIDE CHILDREN'S HOSPITAL
<120> ADENO-ASSOCIATED VIRUS VECTOR DELIVERY OF A FRAGMENT OF
      MICRO-DYSTROPHIN TO TREAT MUSCULAR DYSTROPHY
<130> 28335/50217A PC
<150> US 62/473,255
<151> 2017-03-17
<160> 4
<170> PatentIn version 3.5
<210> 1
<211> 3275
<212> DNA
<213> Adeno-Associated Virus
<400> 1
atgctttggt gggaagaagt agaggactgt tatgaaagag aagatgttca aaagaaaaca    60
ttcacaaaat gggtaaatgc acaattttct aagtttggga agcagcatat tgagaacctc   120
ttcagtgacc tacaggatgg gaggcgcctc ctagacctcc tcgaaggcct gacagggcaa   180
aaactgccaa aagaaaaagg atccacaaga gttcatgccc tgaacaatgt caacaaggca   240
ctgcgggttt tgcagaacaa taatgttgat ttagtgaata ttggaagtac tgacatcgta   300
gatggaaatc ataaactgac tcttggtttg atttggaata taatcctcca ctggcaggtc   360
aaaaatgtaa tgaaaaatat catggctgga ttgcaacaaa ccaacagtga aaagattctc   420
ctgagctggg tccgacaatc aactcgtaat tatccacagg ttaatgtaat caacttcacc   480
accagctggt ctgatggcct ggctttgaat gctctcatcc atagtcatag gccagaccta   540
tttgactgga atagtgtggt ttgccagcag tcagccacac aacgactgga acatgcattc   600
aacatcgcca gatatcaatt aggcatagag aaactactcg atcctgaaga tgttgatacc   660
acctatccag ataagaagtc catcttaatg tacatcacat cactcttcca agttttgcct   720
caacaagtga gcattgaagc catccaggaa gtggaaatgt tgccaaggcc acctaaagtg   780
actaaagaag aacattttca gttacatcat caaatgcact attctcaaca gatcacggtc   840
```

```
agtctagcac agggatatga gagaacttct tccccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaaaac   1260
ctcagcactc tggaagacct gaacaccaga tggaagcttc tgcaggtggc cgtcgaggac   1320
cgagtcaggc agctgcatga agcccacagg gactttggtc cagcatctca gcactttctt   1380
tccacgtctg tccagggtcc ctgggagaga gccatctcgc caaacaaagt gccctactat   1440
atcaaccacg agactcaaac aacttgctgg gaccatccca aaatgacaga gctctaccag   1500
tctttagctg acctgaataa tgtcagattc tcagcttata ggactgccat gaaactccga   1560
agactgcaga aggccctttg cttggatctc ttgagcctgt cagctgcatg tgatgccttg   1620
gaccagcaca acctcaagca aaatgaccag cccatggata tcctgcagat tattaattgt   1680
ttgaccacta tttatgaccg cctggagcaa gagcacaaca atttggtcaa cgtccctctc   1740
tgcgtggata tgtgtctgaa ctggctgctg aatgtttatg atacgggacg aacagggagg   1800
atccgtgtcc tgtcttttaa aactggcatc atttccctgt gtaaagcaca tttggaagac   1860
aagtacagat accttttcaa gcaagtggca agttcaacag gattttgtga ccagcgcagg   1920
ctgggcctcc ttctgcatga ttctatccaa attccaagac agttgggtga agttgcatcc   1980
tttgggggca gtaacattga gccaagtgtc cggagctgct tccaatttgc taataataag   2040
ccagagatcg aagcggccct cttcctagac tggatgagac tggaaccca gtccatggtg   2100 tggctgcccg tcctgcacag agtggctgct gcagaaactg ccaagcatca ggccaaatgt   2160
aacatctgca aagagtgtcc aatcattgga ttcaggtaca ggagtctaaa gcactttaat   2220
tatgacatct gccaaagctg cttttttttct ggtcgagttg caaaaggcca taaaatgcac   2280
tatcccatgg tggaatattg cactccgact acatcaggag aagatgttcg agactttgcc   2340
aaggtactaa aaaacaaatt tcgaaccaaa aggtattttg cgaagcatcc ccgaatgggc   2400
tacctgccag tgcagactgt cttagagggg acaacatgg aaactcccgt tactctgatc   2460
aacttctggc cagtagattc tgcgcctgcc tcgtcccctc agctttcaca cgatgatact   2520
cattcacgca ttgaacatta tgctagcagg ctagcagaaa tggaaaacag caatggatct   2580
tatctaaatg atagcatctc tcctaatgag agcatagatg atgaacattt gttaatccag   2640
cattactgcc aaagtttgaa ccaggactcc cccctgagcc agcctcgtag tcctgcccag   2700
atcttgattt ccttagagag tgaggaaaga ggggagctag agagaatcct agcagatctt   2760
gaggaagaaa acaggaatct gcaagcagaa tatgaccgtc taaagcagca gcacgaacat   2820
aaaggcctgt ccccactgcc gtccctcct gaaatgatgc ccacctctcc ccagagtccc   2880
cgggatgctg agctcattgc tgaggccaag ctactgcgtc aacacaaagg ccgcctggaa   2940
gccaggatgc aaatcctgga agaccacaat aaacagctgg agtcacagtt acacaggcta   3000
aggcagctgc tggagcaacc ccaggcagag gccaaagtga atggcacaac ggtgtcctct   3060
ccttctacct ctctacagag gtccgacagc agtcagccta tgctgctccg agtggttggc   3120
```

SEQUENCE LISTING

```
agtcaaactt cggactccat gggtgaggaa gatcttctca gtcctcccca ggacacaagc    3180
acagggttag aggaggtgat ggagcaactc aacaactcct tccctagttc aagaggaaga    3240 aataccctg gaaagccaat gagagaggac acaat                                3275
<210> 2
<211> 8329
<212> DNA
<213> Adeno-Associated Virus
<220>
<221> misc_feature
<222> (4497)...(4502)
<223> n is a, c, g, or t
<220>
<221> misc_feature
<222> (8147)...(8152)
<223> n is a, c, g, or t
<400> 2
atctatgtct agagtttaaa caagcttgca tgtctaagct agacccttca gattaaaaat     60
aactgaggta agggcctggg taggggaggt ggtgtgagac gctcctgtct ctcctctatc    120
tgcccatcgg ccctttgggg aggaggaatg tgcccaagga ctaaaaaaag gccatggagc    180
cagaggggcg agggcaacag acctttcatg gcaaaccttg gggccctgc tgtctagcat    240 gccccactac gggtctaggc tgcccatgta aggaggcaag gctggggac acccgagatg    300 cctggttata attaacccag acatgtggct gccccccccc ccccaacacc tgctgcctct    360
aaaaataacc ctgtccctgg tggatcccct gcatgcgaag atcttcgaac aaggctgtgg    420
gggactgagg gcaggctgta acaggcttgg gggccagggc ttatacgtgc ctgggactcc    480
caaagtatta ctgttccatg ttcccggcga agggccagct gtccccgcc agctagactc    540 agcacttagt ttaggaacca gtgagcaagt cagcccttgg ggcagcccat acaaggccat    600
ggggctgggc aagctgcacg cctgggtccg ggtgggcac ggtgcccggg caacgagctg    660
aaagctcatc tgctctcagg ggcccctccc tggggacagc ccctcctggc tagtcacacc    720
ctgtaggctc ctctatataa cccaggggca ctggtgctgc cctcattcta ccaccacctc    780
cacagcacag acagacactc aggagcagcc agcggcgcgc ccaggtaagt ttagtctttt    840
tgtcttttat ttcaggtccc ggatccggtg gtggtgcaaa tcaaagaact gctcctcagt    900
ggatgttgcc tttacttcta ggcctgtacg gaagtgttac ttctgctcta aaagctgcgg    960
aattgtaccc gcggccgcat gctttggtgg aagaagtag aggactgtta tgaaagagaa   1020
gatgttcaaa agaaaacatt cacaaaatgg gtaaatgcac aattttctaa gtttgggaag   1080
cagcatattg agaacctctt cagtgaccta caggatggga ggcgcctcct agacctcctc   1140
gaaggcctga cagggcaaaa actgccaaaa gaaaaaggat ccacaagagt tcatgccctg   1200
aacaatgtca acaaggcact gcgggttttg cagaacaata atgttgattt agtgaatatt   1260
ggaagtactg acatcgtaga tggaaatcat aaactgactc ttggtttgat ttggaatata   1320
atcctccact ggcaggtcaa aaatgtaatg aaaaatatca tggctggatt gcaacaaacc   1380
aacagtgaaa agattctcct gagctgggtc cgacaatcaa ctcgtaatta ccacaggtt   1440 aatgtaatca acttcaccac cagctggtct gatggcctgg ctttgaatgc tctcatccat   1500
agtcataggc cagacctatt tgactggaat agtgtggttt gccagcagtc agccacacaa   1560
cgactggaac atgcattcaa catcgccaga tatcaattag gcatagagaa actactcgat   1620
cctgaagatg ttgataccac ctatccagat aagaagtcca tcttaatgta catcacatca   1680
ctcttccaag ttttgcctca acaagtgagc attgaagcca tccaggaagt ggaaatgttg   1740
ccaaggccac ctaaagtgac taaagaagaa cattttcagt tacatcatca aatgcactat   1800
```

```
SEQUENCE LISTING tctcaacaga tcacggtcag tctagcacag ggatatgaga gaacttcttc ccctaagcct    1860
cgattcaaga gctatgccta cacacaggct gcttatgtca ccacctctga ccctacacgg    1920
agcccatttc cttcacagca tttggaagct cctgaagaca agtcatttgg cagttcattg    1980
atggagagtg aagtaaacct ggaccgttat caaacagctt tagaagaagt attatcgtgg    2040
cttctttctg ctgaggacac attgcaagca caggagaga tttctaatga tgtggaagtg    2100
gtgaaagacc agtttcatac tcatgagggg tacatgatgg atttgacagc ccatcagggc    2160
cgggttggta atattctaca attgggaagt aagctgattg gaacaggaaa attatcagaa    2220
gatgaagaaa ctgaaaacct cagcactctg gaagacctga acaccagatg gaagcttctg    2280
caggtggccg tcgaggaccg agtcaggcag ctgcatgaag cccacaggga ctttggtcca    2340
gcatctcagc actttctttc cacgtctgtc cagggtccct gggagagagc catctcgcca    2400
aacaaagtgc cctactatat caaccacgag actcaaacaa cttgctggga ccatcccaaa    2460
atgacagagc tctaccagtc tttagctgac ctgaataatg tcagattctc agcttatagg    2520
actgccatga aactccgaag actgcagaag gcccttttgct tggatctctt gagcctgtca    2580
gctgcatgtg atgccttgga ccagcacaac ctcaagcaaa atgaccagcc catggatatc    2640
ctgcagatta ttaattgttt gaccactatt tatgaccgcc tggagcaaga gcacaacaat    2700
ttggtcaacg tccctctctg cgtggatatg tgtctgaact ggctgctgaa tgtttatgat    2760 acggacgaa cagggaggat ccgtgtcctg tcttttaaaa ctggcatcat ttccctgtgt    2820
aaagcacatt tggaagacaa gtacagatac cttttcaagc aagtggcaag ttcaacagga    2880
ttttgtgacc agcgcaggct gggcctcctt ctgcatgatt ctatccaaat tccaagacag    2940
ttgggtgaag ttgcatcctt tgggggcagt aacattgagc caagtgtccg gagctgcttc    3000
caatttgcta ataataagcc agagatcgaa gcggccctct tcctagactg gatgagactg    3060
gaaccccagt ccatggtgtg gctgcccgtc ctgcacagag tggctgctgc agaaactgcc    3120
aagcatcagg ccaaatgtaa catctgcaaa gagtgtccaa tcattggatt caggtacagg    3180
agtctaaagc actttaatta tgacatctgc caaagctgct ttttttctgg tcgagttgca    3240
aaaggccata aaatgcacta tcccatggtg gaatattgca ctccgactac atcaggagaa    3300
gatgttcgag actttgccaa ggtactaaaa aacaaatttc gaaccaaaag gtattttgcg    3360
aagcatcccc gaatgggcta cctgccagtg cagactgtct tagagggga caacatggaa    3420 actcccgtta ctctgatcaa cttctggcca gtagattctg cgcctgcctc gtcccctcag    3480
ctttcacacg atgatactca ttcacgcatt gaacattatg ctagcaggct agcagaaatg    3540
gaaaacagca atgatctta tctaaatgat agcatctctc ctaatgagag catagatgat    3600
gaacatttgt taatccagca ttactgccaa agtttgaacc aggactcccc cctgagccag    3660
cctcgtagtc ctgcccagat cttgatttcc ttagagagtg aggaaagagg ggagctagag    3720
agaatcctag cagatcttga ggaagaaaac aggaatctgc aagcagaata tgaccgtcta    3780
aagcagcagc acgaacataa aggcctgtcc ccactgccgt ccctcctga aatgatgccc    3840 acctctcccc agagtccccg ggatgctgag ctcattgctg aggccaagct actgcgtcaa    3900
cacaaaggcc gcctggaagc caggatgcaa atcctggaag accacaataa acagctggag    3960
tcacagttac acaggctaag gcagctgctg gagcaacccc aggcagaggc caaagtgaat    4020
ggcacaacgg tgtcctctcc ttctacctct ctacagaggt ccgacagcag tcagcctatg    4080
```

| | |
|---|---|
| ctgctccgag tggttggcag tcaaacttcg gactccatgg gtgaggaaga tcttctcagt | 4140 |
| cctccccagg acacaagcac agggttagag gaggtgatgg agcaactcaa caactccttc | 4200 |
| cctagttcaa gaggaagaaa taccc ctgga aagccaatga gagaggacac aatgcggccg | 4260 |
| caataaaaga tctttatttt cattagatct gtgtgttggt ttttgtgtg tgtgtgtcta | 4320 |
| gacatggcta cgtagataat tagcatggcg ggttaatcat taactacaag gaaccc ctag | 4380 |
| tgatggagtt ggccactccc tctctgcgcg ctcgctcgct cactgaggcc gggcgaccaa | 4440 |
| aggtcgcccg acgccgggc tttgcccggg cggcctcagt gagcgagcga gcgcgcnnnn | 4500 |
| nncagctggc gtaatagcga agaggcccgc accgatcgcc cttcccaaca gttgcgcagc | 4560 |
| ctgaatggcg aatggaagtt ccagacgatt gagcgtcaaa atgtaggtat tccatgagc | 4620 |
| gttttt cctg ttgcaatggc tggcggtaat attgttctgg atattaccag caaggccgat | 4680 |
| agtttgagtt cttctactca ggcaagtgat gttattacta atcaaagaag tattgcgaca | 4740 |
| acggttaatt tgcgtgatgg acagactctt ttactcggtg gcctcactga ttataaaaac | 4800 |
| acttctcagg attctggcgt accgttcctg tctaaaatcc ctttaatcgg cctcctgttt | 4860 |
| agctcccgct ctgattctaa cgaggaaagc acgttatacg tgctcgtcaa agcaaccata | 4920 |
| gtacgcgccc tgtagcggcg cattaagcgc ggcgggtgtg gtggttacgc gcagcgtgac | 4980 |
| cgctacactt gccagcgccc tagcgcccgc tcctttcgct ttcttccctt cctttctcgc | 5040 |
| cacgttcgcc ggctttcccc gtcaagctct aaatcggggg ctcccttt ag ggttccgatt | 5100 |
| tagtgattta cggcacctcg acccc aaaaa acttgattag ggtgatggtt cacgtagtgg | 5160 |
| gccatcgccc tgatagacgg ttttt cgccc tttgacgttg gagtccacgt tctttaatag | 5220 |
| tggactcttg ttccaaactg gaacaacact caaccc tatc tcggtctatt cttttgattt | 5280 |
| ataagggatt ttgccgattt cggcctattg gttaaaaaat gagctgattt aacaaaaatt | 5340 |
| taacgcgaat tttaacaaaa tattaacgtt tacaatttaa atatttgctt atacaatctt | 5400 |
| cctgtttttg gggcttttct gattatcaac cggggtacat atgattgaca tgctagtttt | 5460 |
| acgattaccg ttcatcgatt ctcttgtttg ctccagactc tcaggcaatg acctgatagc | 5520 |
| ctttgtagag acctctcaaa aatagctacc ctctccggca tgaatttatc agctagaacg | 5580 |
| gttgaatatc atattgatgg tgatttgact gtctccggcc tttctcaccc gtttgaatct | 5640 |
| ttacctacac attactcagg cattgcattt aaaatatatg agggttctaa aaatttttat | 5700 |
| ccttgcgttg aaataaaggc ttctcccgca aaagtattac agggtcataa tgttttt ggt | 5760 |
| acaaccgatt tagctttatg ctctgaggct ttattgctta attttgctaa ttcttttgcct | 5820 |
| tgcctgtatg atttattgga tgttggaagt tcctgatgcg gtattttctc cttacgcatc | 5880 |
| tgtgcggtat ttcacaccgc atatggtgca ctctcagtac aatctgctct gatgccgcat | 5940 |
| agttaagcca gccccgacac ccgccaacac ccgctgacgc gccctgacgg gcttgtctgc | 6000 |
| tcccggcatc cgcttacaga caagctgtga ccgtctccgg gagctgcatg tgtcagaggt | 6060 |
| tttcaccgtc atcaccgaaa cgcgcgagac gaaagggcct cgtgatacgc ctatttttat | 6120 |
| aggttaatgt catgataata atggtttctt agacgtcagg tggcacttt cggggaaatg | 6180 |
| tgcgcggaac ccctatttgt ttatttttct aaatacattc aaatatgtat ccgctcatga | 6240 |
| gacaataacc ctgataaatg cttcaataat attgaaaaag gaagagtatg agtattcaac | 6300 |
| atttccgtgt cgcccttatt cccttttttg cggcattttg ccttcctgtt tttgctcacc | 6360 |
| cagaaacgct ggtgaaagta aaagatgctg aagatcagtt gggtgcacga gtgggttaca | 6420 |

```
tcgaactgga tctcaacagc ggtaagatcc ttgagagttt tcgccccgaa gaacgttttc    6480
caatgatgag cacttttaaa gttctgctat gtggcgcggt attatcccgt attgacgccg    6540
ggcaagagca actcggtcgc cgcatacact attctcagaa tgacttggtt gagtactcac    6600
cagtcacaga aaagcatctt acggatggca tgacagtaag agaattatgc agtgctgcca    6660
taaccatgag tgataacact gcggccaact tacttctgac aacgatcgga ggaccgaagg    6720
agctaaccgc ttttttgcac aacatggggg atcatgtaac tcgccttgat cgttgggaac    6780
cggagctgaa tgaagccata ccaaacgacg agcgtgacac cacgatgcct gtagcaatgg    6840
caacaacgtt gcgcaaacta ttaactggcg aactacttac tctagcttcc cggcaacaat    6900
taatagactg gatggaggcg gataaagttg caggaccact tctgcgctcg gcccttccgg    6960
ctggctggtt tattgctgat aaatctggag ccggtgagcg tgggtctcgc ggtatcattg    7020
cagcactggg gccagatggt aagccctccc gtatcgtagt tatctacacg acggggagtc    7080
aggcaactat ggatgaacga atagacaga tcgctgagat aggtgcctca ctgattaagc     7140
attggtaact gtcagaccaa gtttactcat atatacttta gattgattta aaacttcatt    7200
tttaatttaa aaggatctag gtgaagatcc tttttgataa tctcatgacc aaaatccctt    7260
aacgtgagtt ttcgttccac tgagcgtcag accccgtaga aaagatcaaa ggatcttctt    7320
gagatccttt ttttctgcgc gtaatctgct gcttgcaaac aaaaaaacca ccgctaccag    7380
cggtggtttg tttgccggat caagagctac caactctttt tccgaaggta actggcttca    7440
gcagagcgca gataccaaat actgtccttc tagtgtagcc gtagttaggc caccacttca    7500
agaactctgt agcaccgcgt atacccctcg ctctgctaat cctgttacca gtggctgctg    7560
ccagtggcga taagtcgtgt cttaccgggt tggactcaag acgatagtta ccggataagg    7620
cgcagcggtc gggctgaacg gggggttcgt gcacacagcc cagcttggag cgaacgacct    7680
acaccgaact gagatacctac agcgtgagc tatgagaaag cgccacgctt cccgaaggga    7740
gaaaggcgga caggtatccg gtaagcggca gggtcggaac aggagagcgc acagggagc    7800 ttccaggggg aaacgcctgg tatctttata gtcctgtcgg gtttcgccac ctctgacttg    7860
agcgtcgatt tttgtgatgc tcgtcagggg ggcggagcct atggaaaaac gccagcaacg    7920
cggccttttt acgttcctg gccttttgct ggccttttgc tcacatgttc tttcctgcgt    7980
tatcccctga ttctgtggat aaccgtatta ccgggtttga gtgagctgat accgctcgcc    8040
gcagccgaac gaccgagcgc agcgagtcag tgagcgacca gcggaagag cgcccaatac    8100 gcaaaccgcc tctccccgcg cgttggccga ttcattaatg cagctgnnnn nngcgcgctc    8160
gctcgctcac tgaggccgcc cgggcaaagc ccgggcgtcg ggcgacctt ggtcgcccgg    8220 cctcagtgag cgagcgagcg cgcagagagg gagtggccaa ctccatcact aggggttcct    8280
tgtagttaat gattaacccg ccatgctaat tatctacgta gccatgtct                8329
<210> 3
<211> 730
<212> DNA
<213> Adeno-Associate Virus
<400> 3
aagcttgcat gtctaagcta gacccttcag attaaaaata actgaggtaa gggcctgggt      60
aggggaggtg gtgtgagacg ctcctgtctc tcctctatct gcccatcggc cctttgggga    120
ggaggaatgt gcccaaggac taaaaaaagg ccatggagcc agaggggcga gggcaacaga    180
cctttcatgg gcaaaccttg gggccctgct gtctagcatg ccccactacg ggtctaggct    240
```

SEQUENCE LISTING

```
gcccatgtaa ggaggcaagg cctggggaca cccgagatgc ctggttataa ttaacccaga      300
catgtggctg cccccccccc cccaacacct gctgcctcta aaaataaccc tgtccctggt      360
ggatcccctg catgcgaaga tcttcgaaca aggctgtggg ggactgaggg caggctgtaa      420
caggcttggg ggccagggct tatacgtgcc tgggactccc aaagtattac tgttccatgt      480
tcccggcgaa gggccagctg tccccgcca gctagactca gcacttagtt taggaaccag       540
tgagcaagtc agcccttggg gcagcccata caaggccatg gggctgggca agctgcacgc      600
ctgggtccgg ggtgggcacg gtgcccgggc aacgagctga aagctcatct gctctcaggg      660
gcccctccct ggggacagcc cctcctggct agtcacaccc tgtaggctcc tctatataac      720
ccaggggcac                                                              730
<210> 4
<211> 564
<212> DNA
<213> Adeno-Associated Virus
<400> 4
cagccactat gggtctaggc tgcccatgta aggaggcaag gcctgggac acccgagatg        60 cctggttata attacccag acatgtggct gctccccccc cccaacacct gctgcctgag        120 cctcacccccc accccggtgc ctgggtctta ggctctgtac accatggagg agaagctcgc     180
tctaaaaata accctgtccc tggtgggctg tggggggactg agggcaggct gtaacaggct     240
tgggggccag ggcttatacg tgcctgggac tcccaaagta ttactgttcc atgttcccgg      300
cgaagggcca gctgtccccc gccagctaga ctcagcactt agtttaggaa ccagtgagca      360 agtcagcccct tggggcagcc catacaaggc catgggctg gcaagctgc acgcctgggt       420 ccggggtggg cacggtgccc gggcaacgag ctgaaagctc atctgctctc aggggcccct     480
ccctggggac agcccctcct ggctagtcac accctgtagg ctcctctata acccaggg       540 gcacaggggc tgcccccggg tcac                                             564
```

SEQUENCE LISTING

<160> NUMBER OF SEQ ID NOS: 4

<210> SEQ ID NO 1
<211> LENGTH: 3275
<212> TYPE: DNA
<213> ORGANISM: Adeno-Associated Virus

<400> SEQUENCE: 1

```
atgctttggt gggaagaagt agaggactgt tatgaaagag aagatgttca aaagaaaaca       60
ttcacaaaat gggtaaatgc acaatttttct aagtttggga agcagcatat tgagaacctc     120
ttcagtgacc tacaggatgg gaggcgcctc ctagacctcc tcgaaggcct gacagggcaa      180
aaactgccaa agaaaaagg atccacaaga gttcatgccc tgaacaatgt caacaaggca      240
ctgcgggttt tgcagaacaa taatgttgat ttagtgaata ttggaagtac tgacatcgta      300
gatggaaatc ataaactgac tcttggtttg atttggaata taatcctcca ctggcaggtc      360
aaaaatgtaa tgaaaatat catggctgga ttgcaacaaa ccaacagtga aaagattctc     420
ctgagctggg tccgacaatc aactcgtaat tatccacagg ttaatgtaat caacttcacc      480
accagctggt ctgatggcct ggctttgaat gctctcatcc atagtcatag gccagaccta      540
tttgactgga atagtgtggt ttgccagcag tcagccacac aacgactgga acatgcattc      600
```

-continued

```
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaaaac   1260
ctcagcactc tggaagacct gaacaccaga tggaagcttc tgcaggtggc cgtcgaggac   1320
cgagtcaggc agctgcatga agcccacagg gactttggtc cagcatctca gcactttctt   1380
tccacgtctg tccagggtcc ctgggagaga gccatctcgc caaacaaagt gccctactat   1440
atcaaccacg agactcaaac aacttgctgg gaccatccca aaatgacaga gctctaccag   1500
tctttagctg acctgaataa tgtcagattc tcagcttata ggactgccat gaaactccga   1560
agactgcaga aggccctttg cttggatctc ttgagcctgt cagctgcatg tgatgccttg   1620
gaccagcaca acctcaagca aaatgaccag cccatggata tcctgcagat tattaattgt   1680
ttgaccacta tttatgaccg cctggagcaa gagcacaaca atttggtcaa cgtccctctc   1740
tgcgtggata tgtgtctgaa ctggctgctg aatgtttatg atacgggacg aacagggagg   1800
atccgtgtcc tgtcttttaa aactggcatc atttccctgt gtaaagcaca tttggaagac   1860
aagtacagat acctttcaa gcaagtggca agttcaacag gattttgtga ccagcgcagg   1920
ctgggcctcc ttctgcatga ttctatccaa attccaagac agttgggtga agttgcatcc   1980
tttgggggca gtaacattga gccaagtgtc cggagctgct ccaatttgc taataataag   2040 ccagagatcg aagcggccct cttcctagac tggatgagac tggaacccca gtccatggtg   2100
tggctgcccg tcctgcacag agtggctgct gcagaaactg ccaagcatca ggccaaatgt   2160
aacatctgca aagagtgtcc aatcattgga ttcaggtaca ggagtctaaa gcactttaat   2220
tatgacatct gccaaagctg cttttttttct ggtcgagttg caaaaggcca taaaatgcac   2280
tatcccatgg tggaatattg cactccgact acatcaggag aagatgttcg agactttgcc   2340
aaggtactaa aaacaaatt tcgaaccaaa aggtattttg cgaagcatcc ccgaatgggc   2400
tacctgccag tgcagactgt cttagagggg acaacatgg aaactcccgt tactctgatc   2460
aacttctggc cagtagattc tgcgcctgcc tcgtcccctc agctttcaca cgatgatact   2520
cattcacgca ttgaacatta tgctagcagg ctagcagaaa tggaaaacag caatggatct   2580
tatctaaatg atagcatctc tcctaatgag agcatagatg atgaacattt gttaatccag   2640
cattactgcc aaagtttgaa ccaggactcc cccctgagcc agcctcgtag tcctgcccag   2700
atcttgattt ccttagagag tgaggaagga ggggagctag agagaatcct agcagatctt   2760
gaggaagaaa acaggaatct gcaagcagaa tatgaccgtc taaagcagca gcacgaacat   2820
aaaggcctgt ccccactgcc gtcccctcct gaaatgatgc ccacctctcc ccagagtccc   2880
cgggatgctg agctcattgc tgaggccaag ctactgcgtc aacacaaagg ccgcctggaa   2940
gccaggatgc aaatcctgga agaccacaat aaacagctgg agtcacagtt acacaggcta   3000
```

| | | |
|---|---|---|
| aggcagctgc tggagcaacc ccaggcagag gccaaagtga atggcacaac ggtgtcctct | 3060 | |
| ccttctacct ctctacagag gtccgacagc agtcagccta tgctgctccg agtggttggc | 3120 | |
| agtcaaactt cggactccat gggtgaggaa gatcttctca gtcctcccca ggacacaagc | 3180 | |
| acagggttag aggaggtgat ggagcaactc aacaactcct tccctagttc aagaggaaga | 3240 | |
| aataccccctg gaaagccaat gagagaggac acaat | 3275 | |

<210> SEQ ID NO 2
<211> LENGTH: 8329
<212> TYPE: DNA
<213> ORGANISM: Adeno-Associated Virus
<220> FEATURE:
<221> NAME/KEY: misc_feature
<222> LOCATION: (4497)..(4502)
<223> OTHER INFORMATION: n is a, c, g, or t
<220> FEATURE:
<221> NAME/KEY: misc_feature
<222> LOCATION: (8147)..(8152)
<223> OTHER INFORMATION: n is a, c, g, or t

<400> SEQUENCE: 2

| | | |
|---|---|---|
| atctatgtct agagtttaaa caagcttgca tgtctaagct agacccttca gattaaaaat | 60 | |
| aactgaggta agggcctggg taggggaggt ggtgtgagac gctcctgtct ctcctctatc | 120 | |
| tgcccatcgg ccctttgggg aggaggaatg tgcccaagga ctaaaaaaag gccatggagc | 180 | |
| cagaggggcg agggcaacag acctttcatg ggcaaaacctt ggggccctgc tgtctagcat | 240 | |
| gccccactac gggtctaggc tgcccatgta aggaggcaag gcctggggac acccgagatg | 300 | |
| cctggttata attaacccag acatgtggct gccccccccc cccaacacc tgctgcctct | 360 | |
| aaaaataacc ctgtccctgg tggatcccct gcatgcgaag atcttcgaac aaggctgtgg | 420 | |
| gggactgagg gcaggctgta acaggcttgg gggccagggc ttatacgtgc ctgggactcc | 480 | |
| caaagtatta ctgttccatg ttcccggcga agggccagct gtcccccgcc agctagactc | 540 | |
| agcacttagt ttaggaacca gtgagcaagt cagcccttgg ggcagccat acaaggccat | 600 | |
| ggggctgggc aagctgcacg cctgggtccg gggtgggcac ggtgcccggg caacgagctg | 660 | |
| aaagctcatc tgctctcagg ggcccctccc tgggacagc ccctcctggc tagtcacacc | 720 | |
| ctgtaggctc ctctatataa cccaggggca ctggtgctgc cctcattcta ccaccacctc | 780 | |
| cacagcacag acagacactc aggagcagcc agcggcgcgc ccaggtaagt ttagtcttt | 840 | |
| tgtctttat ttcaggtccc ggatccggtg gtggtgcaaa tcaaagaact gctcctcagt | 900 | |
| ggatgttgcc tttacttcta ggcctgtacg gaagtgttac ttctgctcta aaagctgcgg | 960 | |
| aattgtaccc gcggccgcat gctttggtgg gaagaagtag aggactgtta tgaaagagaa | 1020 | |
| gatgttcaaa agaaaacatt cacaaaatgg gtaaatgcac aattttctaa gtttgggaag | 1080 | |
| cagcatattg agaacctctt cagtgaccta caggatggga ggcgcctcct agacctcctc | 1140 | |
| gaaggcctga cagggcaaaa actgccaaaa gaaaaaggat ccacaagagt tcatgccctg | 1200 | |
| aacaatgtca caaggcact gcgggtttttg cagaacaata tgttgatttt agtgaatatt | 1260 | |
| ggaagtactg acatcgtaga tgaaaatcat aaactgactc ttggtttgat ttggaatata | 1320 | |
| atcctccact ggcaggtcaa aaatgtaatg aaaaatatca tggctggatt gcaacaaacc | 1380 | |
| aacagtgaaa agattctcct gagctgggtc cgacaatcaa ctcgtaatta ccacaggtt | 1440 | |
| aatgtaatca acttcaccac cagctggtct gatggcctgg ctttgaatgc tctcatccat | 1500 | |
| agtcataggc cagacctatt tgactggaat agtgtggttt gccagcagtc agccacacaa | 1560 | |

```
cgactggaac atgcattcaa catcgccaga tatcaattag gcatagagaa actactcgat    1620
cctgaagatt ttgataccac ctatccagat aagaagtcca tcttaatgta catcacatca    1680
ctcttccaag ttttgcctca acaagtgagc attgaagcca tccaggaagt ggaaatgttg    1740
ccaaggccac ctaaagtgac taaagaagaa cattttcagt tacatcatca aatgcactat    1800
tctcaacaga tcacggtcag tctagcacag ggatatgaga gaacttcttc ccctaagcct    1860
cgattcaaga gctatgccta cacacaggct gcttatgtca ccacctctga ccctacacgg    1920
agcccatttc cttcacagca tttggaagct cctgaagaca agtcatttgg cagttcattg    1980
atggagagtg aagtaaacct ggaccgttat caaacagctt tagaagaagt attatcgtgg    2040
cttctttctg ctgaggacac attgcaagca caaggagaga tttctaatga tgtggaagtg    2100
gtgaaagacc agtttcatac tcatgagggg tacatgatgg atttgacagc ccatcagggc    2160
cgggttggta atattctaca attgggaagt aagctgattg gaacaggaaa attatcagaa    2220
gatgaagaaa ctgaaaacct cagcactctg gaagacctga acaccagatg gaagcttctg    2280
caggtggccg tcgaggaccg agtcaggcag ctgcatgaag cccacaggga ctttggtcca    2340
gcatctcagc acttctttc cacgtctgtc cagggtccct gggagagagc catctcgcca    2400
aacaaagtgc cctactatat caaccacgag actcaaacaa cttgctggga ccatcccaaa    2460
atgacagagc tctaccagtc tttagctgac ctgaataatg tcagattctc agcttatagg    2520
actgccatga aactccgaag actgcagaag gcccttttgct tggatctctt gagcctgtca    2580
gctgcatgtg atgccttgga ccagcacaac ctcaagcaaa atgaccagcc catggatatc    2640
ctgcagatta ttaattgttt gaccactatt tatgaccgcc tggagcaaga gcacaacaat    2700
ttggtcaacg tccctctctg cgtggatatg tgtctgaact ggctgctgaa tgtttatgat    2760
acgggacgaa cagggaggat ccgtgtcctg tcttttaaaa ctggcatcat ttccctgtgt    2820
aaagcacatt tggaagacaa gtacagatac cttttcaagc aagtggcaag ttcaacagga    2880 tttttgtgacc agcgcaggct gggcctcctt ctgcatgatt ctatccaaat tccaagacag    2940
ttgggtgaag ttgcatcctt tgggggcagt aacattgagc caagtgtccg gagctgcttc    3000
caatttgcta ataataagcc agagatcgaa gcggccctct tcctagactg gatgagactg    3060
gaaccccagt ccatggtgtg gctgcccgtc ctgcacagag tggctgctgc agaaactgcc    3120
aagcatcagg ccaaatgtaa catctgcaaa gagtgtccaa tcattggatt caggtacagg    3180
agtctaaagc actttaatta tgacatctgc caaagctgct tttttttctgg tcgagttgca    3240 aaaggccata aaatgcacta tcccatggtg gaatattgca ctccgactac atcaggagaa    3300
gatgttcgag acttttgccaa ggtactaaaa aacaaatttc gaaccaaaag gtattttgcg    3360
aagcatcccc gaatgggcta cctgccagtg cagactgtct tagaggggga caacatggaa    3420
actcccgtta ctctgatcaa cttctggcca gtagattctg cgcctgcctc gtcccctcag    3480
ctttcacacg atgatactca ttcacgcatt gaacattatg ctagcaggct agcagaaatg    3540
gaaaacagca atggatctta tctaaatgat agcatctctc ctaatgagag catagatgat    3600
gaacatttgt taatccagca ttactgccaa agtttgaacc aggactcccc cctgagccag    3660
cctcgtagtc ctgcccagat cttgatttcc ttagagagtg aggaaagagg ggagctagag    3720
agaatcctag cagatcttga ggaagaaaac aggaatctgc aagcagaata tgaccgtcta    3780
aagcagcagc acgaacataa aggcctgtcc ccactgccgt cccctcctga aatgatgccc    3840
acctctcccc agagtcccgg ggatgctgag ctcattgctg aggccaagct actgcgtcaa    3900
cacaaaggcc gcctggaagc caggatgcaa atcctggaag accacaataa acagctggag    3960
```

```
tcacagttac acaggctaag gcagctgctg gagcaacccc aggcagaggc caaagtgaat    4020
ggcacaacgg tgtcctctcc ttctacctct ctacagaggt ccgacagcag tcagcctatg    4080
ctgctccgag tggttggcag tcaaacttcg gactccatgg gtgaggaaga tcttctcagt    4140
cctccccagg acacaagcac agggttagag gaggtgatgg agcaactcaa caactccttc    4200
cctagttcaa gaggaagaaa tacccctgga aagccaatga gagaggacac aatgcggccg    4260
caataaaaga tctttatttt cattagatct gtgtgttggt tttttgtgtg tgtgtgtcta    4320
gacatggcta cgtagataat tagcatggcg ggttaatcat taactacaag gaacccctag    4380
tgatggagtt ggccactccc tctctgcgcg ctcgctcgct cactgaggcc gggcgaccaa    4440
aggtcgcccg acgcccgggc tttgcccggg cggcctcagt gagcgagcga gcgcgcnnnn    4500
nncagctggc gtaatagcga agaggcccgc accgatcgcc cttcccaaca gttgcgcagc    4560
ctgaatggcg aatggaagtt ccagacgatt gagcgtcaaa atgtaggtat ttccatgagc    4620 gttttcctg ttgcaatggc tggcggtaat attgttctgg atattaccag caaggccgat    4680
agtttgagtt cttctactca ggcaagtgat gttattacta atcaaagaag tattgcgaca    4740
acggttaatt tgcgtgatgg acagactctt ttactcggtg gcctcactga ttataaaaac    4800
acttctcagg attctggcgt accgttcctg tctaaaatcc ctttaatcgg cctcctgttt    4860
agctcccgct ctgattctaa cgaggaaagc acgttatacg tgctcgtcaa agcaaccata    4920
gtacgcgccc tgtagcggcg cattaagcgc ggcgggtgtg gtggttacgc gcagcgtgac    4980
cgctacactt gccagcgccc tagcgcccgc tcctttcgct ttcttccctt cctttctcgc    5040
cacgttcgcc ggctttcccc gtcaagctct aaatcggggg ctccctttag ggttccgatt    5100
tagtgattta cggcacctcg accccaaaaa acttgattag ggtgatggtt cacgtagtgg    5160
gccatcgccc tgatagacgg ttttcgccc tttgacgttg gagtccacgt tctttaatag    5220
tggactcttg ttccaaactg gaacaacact caacccctatc tcggtctatt cttttgattt    5280
ataagggatt ttgccgattt cggcctattg gttaaaaaat gagctgattt aacaaaaatt    5340
taacgcgaat tttaacaaaa tattaacgtt tacaatttaa atatttgctt atacaatctt    5400 cctgttttg gggcttttct gattatcaac cggggtacat atgattgaca tgctagtttt    5460
acgattaccg ttcatcgatt ctcttgtttg ctccagactc tcaggcaatg acctgatagc    5520
ctttgtagag acctctcaaa aatagctacc ctctccggca tgaatttatc agctagaacg    5580
gttgaatatc atattgatgg tgatttgact gtctccggcc tttctcaccc gtttgaatct    5640
ttacctacac attactcagg cattgcattt aaaatatatg agggttctaa aaattttat    5700 ccttgcgttg aaataaaggc ttctcccgca aaagtattac agggtcataa tgttttggt    5760 acaaccgatt tagctttatg ctctgaggct ttattgctta atttttgctaa ttctttgcct    5820 tgcctgtatg atttattgga tgttggaagt tcctgatgcg gtattttctc cttacgcatc    5880
tgtgcggtat ttcacaccgc atatggtgca ctctcagtac aatctgctct gatgccgcat    5940
agttaagcca gccccgacac ccgccaacac ccgctgacgc gccctgacgg gcttgtctgc    6000
tcccggcatc cgcttacaga caagctgtga ccgtctccgg gagctgcatg tgtcagaggt    6060
tttcaccgtc atcaccgaaa cgcgcgagac gaaagggcct cgtgatacgc ctattttat    6120 aggttaatgt catgataata atggtttctt agacgtcagg tggcacttt cggggaaatg    6180 tgcgcggaac ccctatttgt ttatttttct aaatacattc aaatatgtat ccgctcatga    6240
gacaataacc ctgataaatg cttcaataat attgaaaaag gaagagtatg agtattcaac    6300
```

```
atttccgtgt cgcccttatt ccctttttg cggcattttg ccttcctgtt tttgctcacc    6360
cagaaacgct ggtgaaagta aaagatgctg aagatcagtt gggtgcacga gtgggttaca   6420
tcgaactgga tctcaacagc ggtaagatcc ttgagagttt tcgccccgaa gaacgttttc   6480
caatgatgag cactttaaa gttctgctat gtggcgcggt attatcccgt attgacgccg    6540
ggcaagagca actcggtcgc cgcatacact attctcagaa tgacttggtt gagtactcac   6600
cagtcacaga aaagcatctt acggatggca tgacagtaag agaattatgc agtgctgcca   6660
taaccatgag tgataacact gcggccaact tacttctgac aacgatcgga ggaccgaagg   6720
agctaaccgc tttttgcac aacatggggg atcatgtaac tcgccttgat cgttgggaac    6780
cggagctgaa tgaagccata ccaaacgacg agcgtgacac cacgatgcct gtagcaatgg   6840
caacaacgtt gcgcaaacta ttaactggcg aactacttac tctagcttcc cggcaacaat   6900
taatagactg gatggaggcg gataaagttg caggaccact tctgcgctcg gcccttccgg   6960
ctggctggtt tattgctgat aaatctggag ccggtgagcg tgggtctcgc ggtatcattg   7020
cagcactggg gccagatggt aagccctccc gtatcgtagt tatctacacg acggggagtc   7080
aggcaactat ggatgaacga atagacaga tcgctgagat aggtgcctca ctgattaagc     7140
attggtaact gtcagaccaa gtttactcat atatacttta gattgattta aaacttcatt   7200
tttaatttaa aaggatctag gtgaagatcc ttttgataa tctcatgacc aaaatccctt    7260
aacgtgagtt ttcgttccac tgagcgtcag accccgtaga aaagatcaaa ggatcttctt   7320
gagatccttt ttttctgcgc gtaatctgct gcttgcaaac aaaaaaacca ccgctaccag   7380
cggtggttg tttgccggat caagagctac caactctttt tccgaaggta actggcttca    7440
gcagagcgca gataccaaat actgtccttc tagtgtagcc gtagttaggc caccacttca   7500
agaactctgt agcaccgcgt acatacctcg ctctgctaat cctgttacca gtggctgctg   7560
ccagtggcga taagtcgtgt cttaccgggt tggactcaag acgatagtta ccggataagg   7620
cgcagcggtc gggctgaacg gggggttcgt gcacacagcc cagcttggag cgaacgacct   7680
acaccgaact gagatacta cagcgtgagc tatgagaaag cgccacgctt cccgaaggga    7740
gaaaggcgga caggtatccg gtaagcggca gggtcggaac aggagagcgc acgagggagc   7800
ttccagggg aaacgcctgg tatctttata gtcctgtcgg gtttcgccac ctctgacttg    7860
agcgtcgatt tttgtgatgc tcgtcagggg gcggagcct atggaaaaac gccagcaacg    7920
cggcctttt acggttcctg gccttttgct ggccttttgc tcacatgttc tttcctgcgt    7980
tatccctga ttctgtggat aaccgtatta ccggtttga gtgagctgat accgctcgcc     8040
gcagccgaac gaccgagcgc agcgagtcag tgagcgacca gcggaagag cgcccaatac    8100
gcaaaccgcc tctccccgcg cgttggccga ttcattaatg cagctgnnnn nngcgcgctc   8160
gctcgctcac tgaggccgcc cgggcaaagc ccgggcgtcg ggcgaccttt ggtcgcccgg   8220
cctcagtgag cgagcgagcg cgcagagagg gagtggccaa ctccatcact aggggttcct   8280
tgtagttaat gattaacccg ccatgctaat tatctacgta gccatgtct              8329
```

<210> SEQ ID NO 3
<211> LENGTH: 730
<212> TYPE: DNA
<213> ORGANISM: Adeno-Associate Virus

<400> SEQUENCE: 3

```
aagcttgcat gtctaagcta gacccttcag attaaaaata actgaggtaa gggcctgggt      60
aggggaggtg gtgtgagacg ctcctgtctc tcctctatct gcccatcggc cctttgggga    120
```

-continued

```
ggaggaatgt gcccaaggac taaaaaaagg ccatggagcc agaggggcga gggcaacaga      180
cctttcatgg gcaaaccttg gggccctgct gtctagcatg ccccactacg ggtctaggct      240
gcccatgtaa ggaggcaagg cctggggaca cccgagatgc ctggttataa ttaacccaga      300
catgtggctg cccccccccc cccaacacct gctgcctcta aaataaccc tgtccctggt       360 ggatcccctg catgcgaaga tcttcgaaca aggctgtggg ggactgaggg caggctgtaa      420
caggcttggg ggcagggct tatacgtgcc tgggactccc aaagtattac tgttccatgt      480
tcccggcgaa gggccagctg tcccccgcca gctagactca gcacttagtt taggaaccag      540
tgagcaagtc agcccttggg gcagcccata caaggccatg gggctgggca agctgcacgc      600
ctgggtccgg ggtgggcacg gtgcccgggc aacgagctga aagctcatct gctctcaggg      660
gcccctccct ggggacagcc cctcctggct agtcacaccc tgtaggctcc tctatataac      720
ccaggggcac                                                             730

<210> SEQ ID NO 4
<211> LENGTH: 564
<212> TYPE: DNA
<213> ORGANISM: Adeno-Associated Virus

<400> SEQUENCE: 4
cagccactat gggtctaggc tgcccatgta aggaggcaag gcctggggac acccgagatg       60
cctggttata attaacccag acatgtggct gctccccccc cccaacacct gctgcctgag      120
cctcaccccc accccggtgc ctgggtctta ggctctgtac accatggagg agaagctcgc      180
tctaaaaata accctgtccc tggtgggctg tgggggactg agggcaggct gtaacaggct      240
tgggggccag ggcttatacg tgcctgggac tcccaaagta ttactgttcc atgttcccgg      300
cgaagggcca gctgtccccc gccagctaga ctcagcactt agtttaggaa ccagtgagca      360
agtcagccct tggggcagcc catacaaggc catggggctg ggcaagctgc acgcctgggt      420
ccggggtggg cacggtgccc gggcaacgag ctgaaagctc atctgctctc aggggcccct      480
ccctggggac agcccctcct ggctagtcac accctgtagg ctcctctata acccaggg       540 gcacagggc tgccccgggt cac                                               564
```

What is claimed:

1. A recombinant AAV vector comprising the nucleotide sequence of SEQ ID NO: 1.

2. The recombinant AAV vector of claim 1 further comprising a muscle specific control element.

3. The recombinant AAV vector of claim 2 wherein the muscle-specific control element is human skeletal actin gene element, cardiac actin gene element, myocyte-specific enhancer binding factor (MEF) element, muscle creatine kinase (MCK), truncated MCK (tMCK), myosin heavy chain (MHC) control element, hybrid α-myosin heavy chain enhancer-/MCK enhancer-promoter (MHCK7), C5-12, murine creatine kinase enhancer element, skeletal fast-twitch troponin C gene element, slow-twitch cardiac troponin C gene element, the slow-twitch troponin I gene element, the hypoxia response element, steroid-inducible element or glucocorticoid response element (GRE).

4. The recombinant AAV vector of claim 2 comprising the AAV genome set out in the nucleotide sequence of SEQ ID NO: 2.

5. The recombinant AAV vector of claim 1 wherein the vector is the serotype AAVrh.74, AAV1, AAV2, AAV4, AAV5, AAV6, AAV7, AAV8, AAV9, AAV10, AAV11, AAV12 or AAV13.

6. A composition comprising the recombinant AAV vector of claim 1 and a carrier.

7. A method of increasing muscular force or muscle mass in a subject suffering from muscular dystrophy comprising administering a therapeutically effective amount of the recombinant AAV vector of claim 1 to the subject.

8. A method of treating muscular dystrophy in a subject in need thereof comprising administering a therapeutically effective amount of the recombinant AAV vector of claim 1 to the subject.

9. The method of claim 7 wherein the muscular dystrophy is Duchenne muscular dystrophy.

10. The method of claim 7 wherein the recombinant AAV vector is administered by intramuscular injection or intravenous injection.

11. The method of claim 7 wherein the recombinant AAV vector is administered systemically.

12. The method of claim 1, where the recombinant AAV vector is parenterally administered by injection, infusion or implantation.

13. The recombinant AAV vector of claim 4 wherein the vector is the serotype AAVrh.74, AAV1, AAV2, AAV4, AAV5, AAV6, AAV7, AAV8, AAV9, AAV10, AAV11, AAV12 or AAV13.

14. A composition comprising the recombinant AAV vector of claim 4 and a carrier.

15. The method of claim 8 wherein the muscular dystrophy is Duchenne muscular dystrophy.

16. The method of claim 8 wherein the recombinant AAV vector is administered by intramuscular injection or intravenous injection.

17. The method of claim 8 wherein the recombinant AAV vector is administered systemically.

18. The method of claim 17, where the recombinant AAV vector is parenterally administered by injection, infusion or implantation.

* * * * *